(12) United States Patent
Green et al.

(10) Patent No.: US 10,433,994 B2
(45) Date of Patent: Oct. 8, 2019

(54) METHODS AND SYSTEMS FOR DELIVERING AN IMPLANT

(71) Applicant: ABBOTT CARDIOVASCULAR SYSTEMS INC., Santa Clara, CA (US)

(72) Inventors: Michael L. Green, Pleasanton, CA (US); Matthew J. Gillick, Murrieta, CA (US)

(73) Assignee: ABBOTT CARDIOVASCULAR SYSTEMS INC., Santa Clara, CA (US)

( * ) Notice: Subject to any disclaimer, the term of this patent is extended or adjusted under 35 U.S.C. 154(b) by 586 days.

(21) Appl. No.: 14/932,830

(22) Filed: Nov. 4, 2015

(65) Prior Publication Data

US 2016/0120680 A1  May 5, 2016

Related U.S. Application Data

(60) Provisional application No. 62/075,059, filed on Nov. 4, 2014.

(51) Int. Cl.
| | | |
|---|---|---|
| *A61F 2/966* | (2013.01) | |
| *F16H 19/04* | (2006.01) | |
| *F16H 57/02* | (2012.01) | |
| *A61F 2/95* | (2013.01) | |

(52) U.S. Cl.
CPC ............. *A61F 2/966* (2013.01); *F16H 19/04* (2013.01); *F16H 57/02* (2013.01); *A61F 2002/9517* (2013.01)

(58) Field of Classification Search
CPC ............. A61F 2/966; A61F 2002/9517; A61B 2017/1205; A61B 17/068
See application file for complete search history.

(56) References Cited

U.S. PATENT DOCUMENTS

| | | |
|---|---|---|
| 3,148,595 A | 9/1964 | Looney |
| 5,344,061 A | 9/1994 | Crainich |
| 5,364,351 A | 11/1994 | Heinzelman et al. |
| 5,443,477 A | 8/1995 | Marin et al. |

(Continued)

FOREIGN PATENT DOCUMENTS

| | | |
|---|---|---|
| EP | 2190388 B1 | 3/2014 |
| WO | WO 2012/068389 A1 | 5/2012 |
| WO | WO 2016/073637 A1 | 5/2016 |

OTHER PUBLICATIONS

U.S. Appl. No. 15/670,719 (US 2017/0333238), filed Aug. 7, 2017 (Nov. 23, 2017).

(Continued)

*Primary Examiner* — Alexander J Orkin
(74) *Attorney, Agent, or Firm* — Baker Botts L.L.P.

(57) ABSTRACT

A system for delivering an implant including a handle, a trigger, and an actuation assembly. The actuation assembly can be configured to displace the outer tubular member in the proximal direction a distance (d) relative to the handle and to separately move the inner shaft member distally a distance (x) relative to the handle upon deployment of the trigger from a first position to a second position, and move the inner shaft member proximally a distance (y) relative to the handle with no displacement of the outer tubular member upon return of the trigger from the second position to the first position.

18 Claims, 27 Drawing Sheets

(56) References Cited

U.S. PATENT DOCUMENTS

| | | | |
|---|---|---|---|
| 5,507,769 A * | 4/1996 | Marin | A61F 2/07 604/104 |
| 5,607,466 A | 3/1997 | Imbert et al. | |
| 5,643,319 A | 7/1997 | Green et al. | |
| 5,707,376 A | 1/1998 | Kavteladze et al. | |
| 5,797,927 A * | 8/1998 | Yoon | A61B 17/0469 606/139 |
| 6,241,758 B1 | 6/2001 | Cox | |
| 6,514,261 B1 * | 2/2003 | Randall | A61F 2/95 604/528 |
| 6,676,693 B1 | 1/2004 | Belding et al. | |
| 6,945,989 B1 | 9/2005 | Betelia et al. | |
| 7,052,511 B2 | 5/2006 | Weldon et al. | |
| 7,326,203 B2 | 2/2008 | Papineau et al. | |
| 7,611,497 B2 | 11/2009 | Wollschlager | |
| 7,758,624 B2 | 7/2010 | Dorn et al. | |
| 7,854,746 B2 | 12/2010 | Dorn et al. | |
| 7,985,250 B2 | 7/2011 | Kaufmann et al. | |
| 8,025,692 B2 | 9/2011 | Feeser | |
| 8,292,939 B2 | 10/2012 | Yachia et al. | |
| 8,382,813 B2 | 2/2013 | Shumer | |
| 8,500,789 B2 | 8/2013 | Wuebbeling et al. | |
| 8,568,467 B2 | 10/2013 | Dorn et al. | |
| 8,603,045 B2 | 12/2013 | Weber | |
| 8,652,193 B2 | 2/2014 | Dorn | |
| 9,039,750 B2 | 5/2015 | Ryan | |
| 9,078,779 B2 | 7/2015 | Dorn et al. | |
| 9,095,465 B2 | 8/2015 | Kelly | |
| 9,149,379 B2 | 10/2015 | Keady et al. | |
| 9,192,500 B1 | 11/2015 | Longo et al. | |
| 2002/0068947 A1 * | 6/2002 | Kuhns | A61B 17/064 606/143 |
| 2003/0028236 A1 | 2/2003 | Gillick et al. | |
| 2003/0191516 A1 | 10/2003 | Weldon et al. | |
| 2005/0080476 A1 * | 4/2005 | Gunderson | A61F 2/95 623/1.11 |
| 2005/0149159 A1 | 7/2005 | Andreas et al. | |
| 2006/0095050 A1 | 5/2006 | Hartley et al. | |
| 2006/0190069 A1 | 8/2006 | Baker-janis et al. | |
| 2007/0156225 A1 | 7/2007 | George et al. | |
| 2007/0250150 A1 | 10/2007 | Pal et al. | |
| 2008/0161902 A1 | 7/2008 | Poulson | |
| 2008/0281336 A1 | 11/2008 | Zergiebel | |
| 2008/0319524 A1 | 12/2008 | Yachia et al. | |
| 2009/0024133 A1 | 1/2009 | Keady et al. | |
| 2010/0174290 A1 | 7/2010 | Wueebbeling | |
| 2011/0295354 A1 | 12/2011 | Bueche et al. | |
| 2012/0029607 A1 | 2/2012 | McHugo et al. | |
| 2012/0053671 A1 | 3/2012 | McHugo et al. | |
| 2012/0158117 A1 | 6/2012 | Ryan | |
| 2012/0172963 A1 | 7/2012 | Ryan et al. | |
| 2012/0221093 A1 | 8/2012 | McHugo | |
| 2012/0290066 A1 | 11/2012 | Nabulsi et al. | |
| 2014/0046428 A1 | 2/2014 | Cragg et al. | |
| 2014/0135909 A1 | 5/2014 | Carr et al. | |
| 2014/0180380 A1 | 6/2014 | Kelly | |
| 2014/0324151 A1 | 10/2014 | Yamashita | |
| 2015/0320971 A1 | 11/2015 | Leeflang et al. | |
| 2016/0120678 A1 * | 5/2016 | Green | A61F 2/966 623/1.11 |

OTHER PUBLICATIONS

U.S. Appl. No. 15/836,649, filed Dec. 8, 2017.
U.S. Appl. No. 29/628,958, filed Dec. 8, 2017.
International Search Report dated Apr. 4, 2018 in International Application No. PCT/US2017/065399.
U.S. Appl. No. 14/560,832, (US 2016/0158049), filed Dec. 4, 2014 (Jun. 9, 2016).
U.S. Appl. No. 14/560,832, dated Apr. 22, 2016 Non-Final Office Action.
U.S. Appl. No. 14/932,875, dated May 19, 2016 Non-Final Office Action.
U.S. Appl. No. 15/835,418, filed Dec. 7, 2017.
U.S. Appl. No. 14/932,795, filed Dec. 26, 2017 Non-Final Office Action.
U.S. Appl. No. 14/932,805, filed Dec. 26, 2017 Non-Final Office Action.
U.S. Appl. No. 14/932,900, filed Jan. 5, 2018 Restriction Requirement.
U.S. Appl. No. 14/932,848, filed Jan. 22, 2018 Restriction Requirement.
U.S. Appl. No. 14/932,862, filed Jan. 22, 2018 Restriction Requirement.
U.S. Appl. No. 14/932,875, filed Jul. 3, 2017 Issue Fee Payment.
U.S. Appl. No. 14/932,875, filed Apr. 5, 2017 Notice of Allowance.
U.S. Appl. No. 14/932,875, filed Mar. 29, 2017 Response after Final Action.
U.S. Appl. No. 14/932,875, filed Mar. 9, 2017 Applicant Initiated Interview Summary.
U.S. Appl. No. 14/932,875, filed Nov. 29, 2016 Final Office Action.
U.S. Appl. No. 14/932,875, filed Aug. 19, 2016 Response to Non-Final Office Action.
U.S. Appl. No. 14/932,875, filed May 19, 2016 Non-Final Office Action.
U.S. Appl. No. 14/560,832, filed Jun. 30, 2017 Issue Fee Payment.
U.S. Appl. No. 14/560,832, filed Mar. 31, 2017 Notice of Allowance.
U.S. Appl. No. 14/560,832, filed Mar. 21, 2017 Response after Final Action.
U.S. Appl. No. 14/560,832, filed Nov. 21, 2016 Final Office Action.
U.S. Appl. No. 14/560,832, filed Aug. 22, 2016 Response to Non-Final Office Action.
U.S. Appl. No. 14/560,832, filed Apr. 22, 2016 Non-Final Office Action.
U.S. Appl. No. 14/932,795, filed Nov. 4, 2015.
U.S. Appl. No. 14/932,805, filed Nov. 4, 2015.
U.S. Appl. No. 14/932,848, filed Nov. 4, 2015.
U.S. Appl. No. 14/932,862, filed Nov. 4, 2015.
U.S. Appl. No. 14/932,875, filed Nov. 4, 2015.
U.S. Appl. No. 14/932,884, filed Nov. 4, 2015.
U.S. Appl. No. 14/932,900, filed Nov. 4, 2015.
International Search report and Written Opinion dated Jan. 29, 2016 in International Application No. PCT/US2015/059070.
International Search report and Written Opinion dated Jan. 29, 2016 in International Application No. PCT/US2015/059074.
International Search report and Written Opinion dated Jan. 29, 2016 in International Application No. PCT/US2015/059084.
U.S. Appl. No. 15/836,649, Jul. 12, 2019, Non-Final Office Action.

* cited by examiner

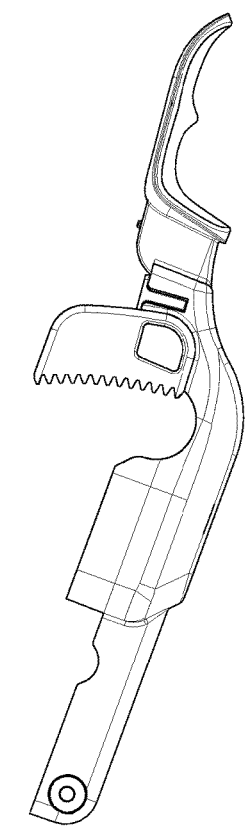
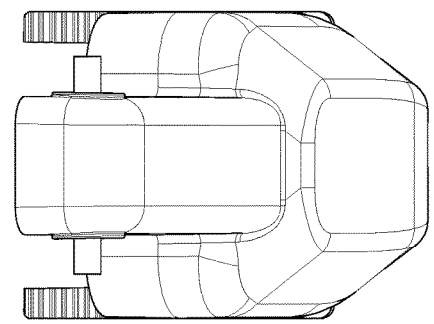
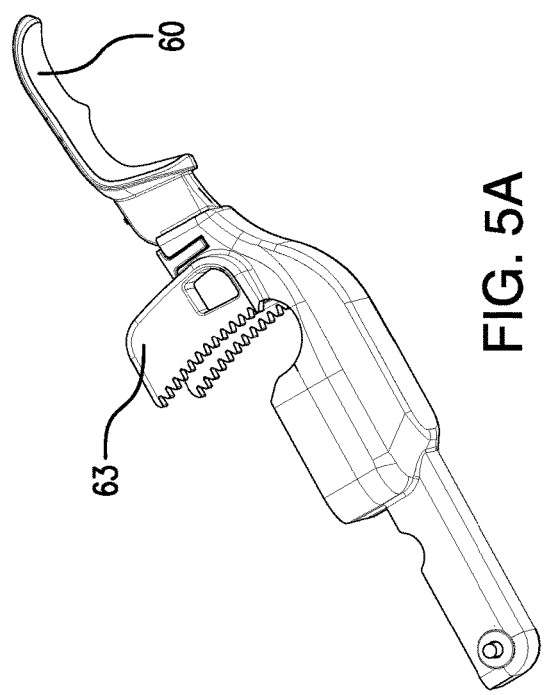
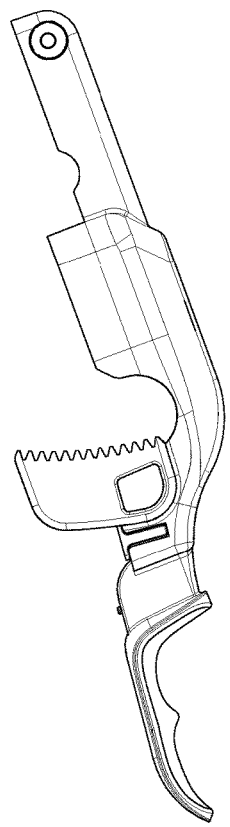
FIG. 5A
FIG. 5B
FIG. 5C
FIG. 5D

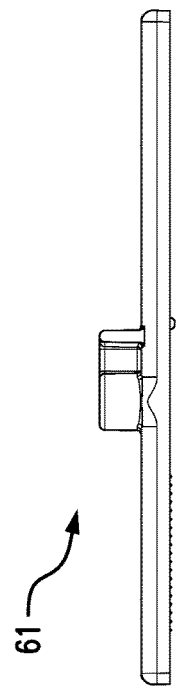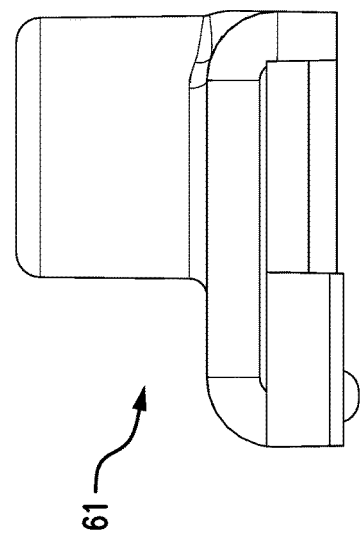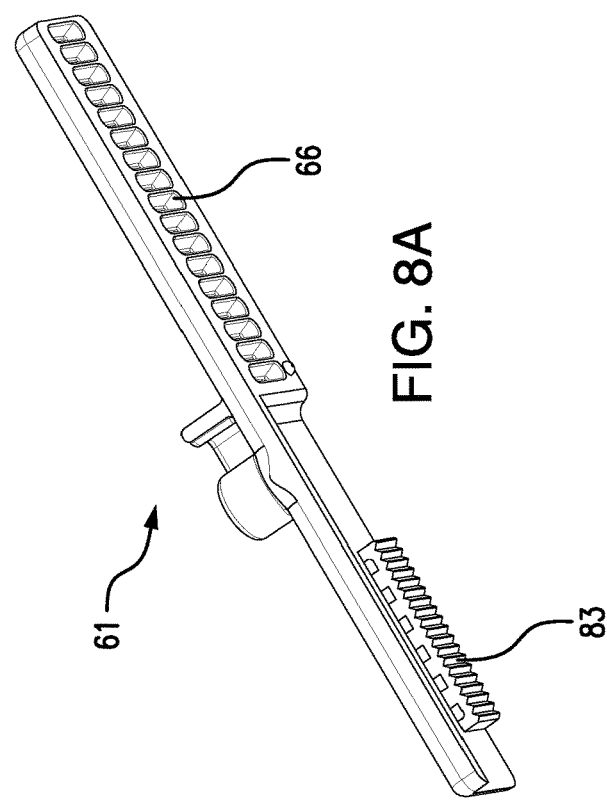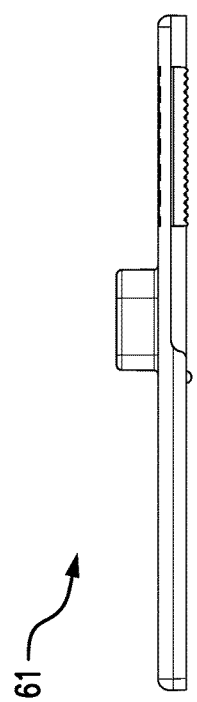

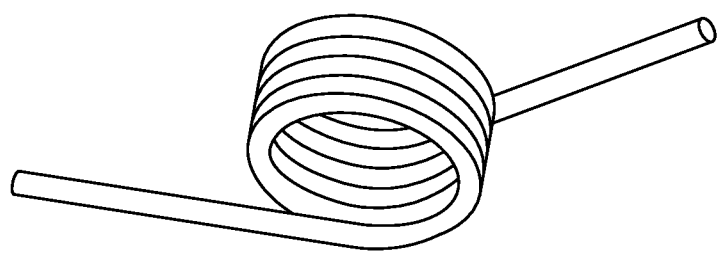
FIG. 11

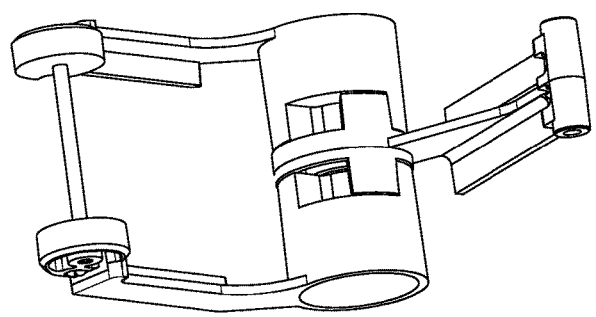
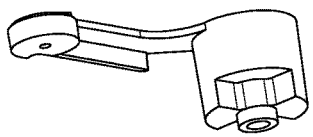
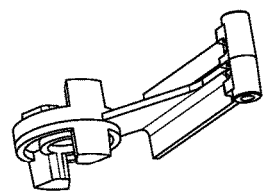
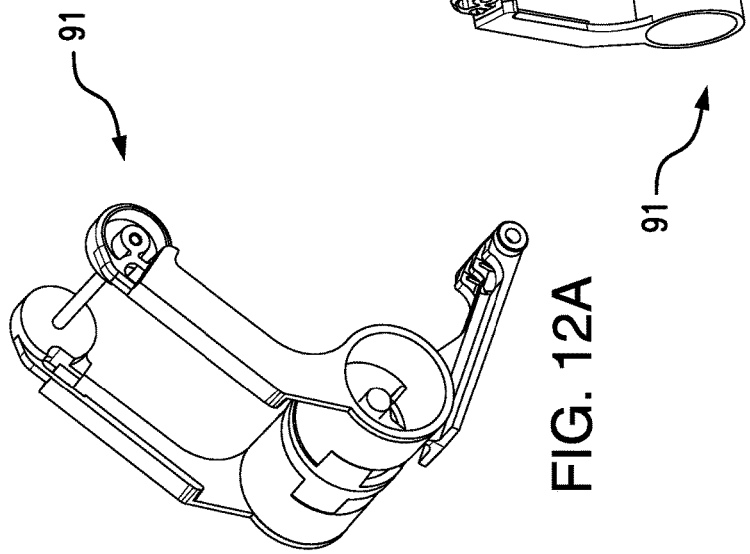
FIG. 12B
FIG. 12C
FIG. 12A

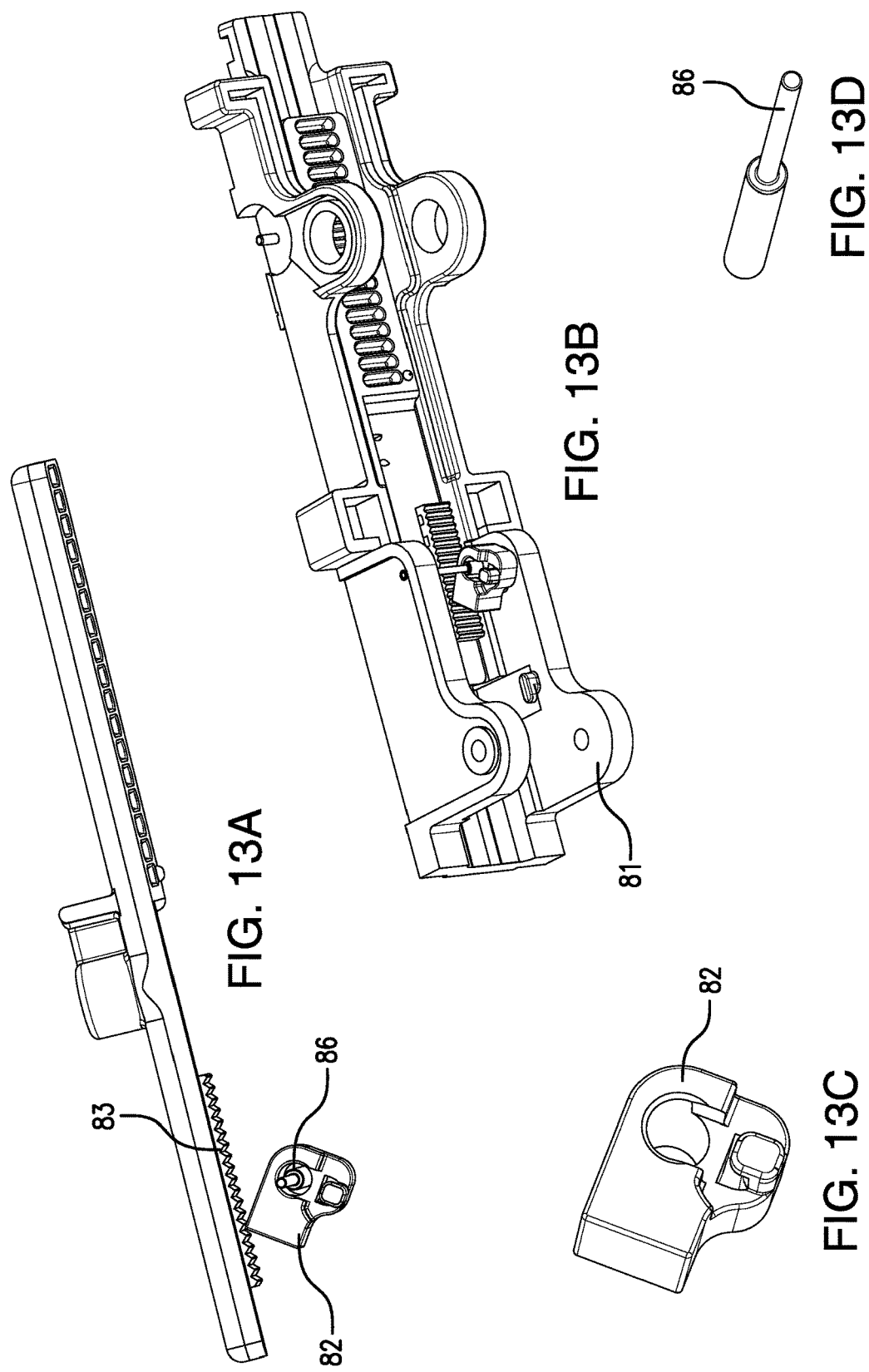

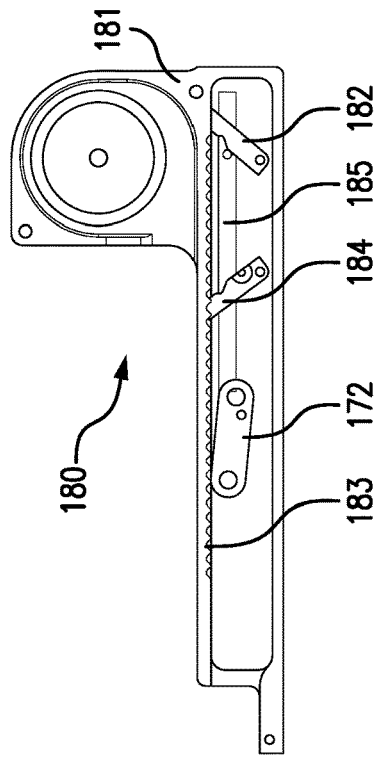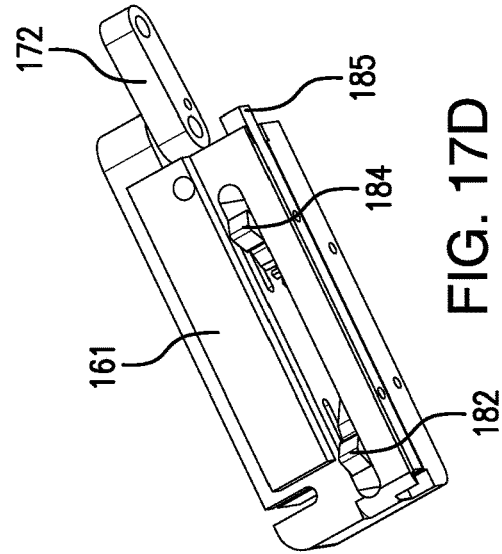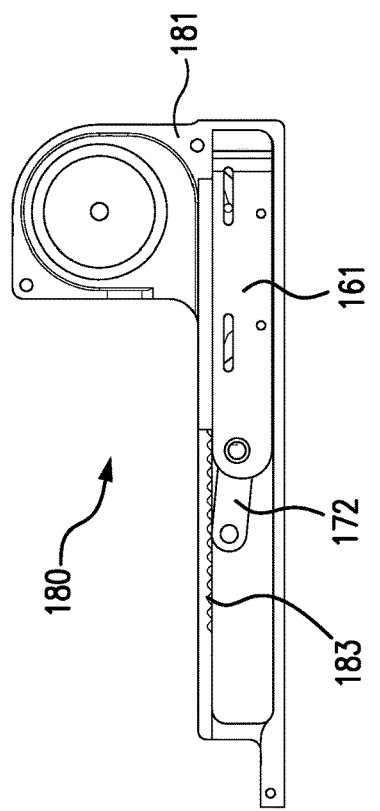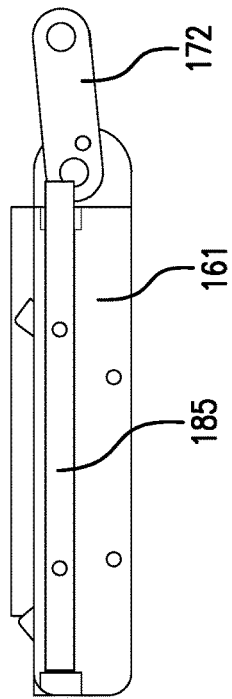

METHODS AND SYSTEMS FOR DELIVERING AN IMPLANT

CROSS REFERENCE TO RELATED APPLICATIONS

The present application claims priority to U.S. Provisional Application No. 62/075,059, filed on Nov. 4, 2014, the entire contents of which is incorporated herein by reference.

BACKGROUND

Field of Disclosed Subject Matter

The disclosed subject matter is directed to systems and methods for delivering one or more medical devices, for example an implant, and more specifically, a braided implant. The braided implant, for example a stent or scaffold, can be disposed within a delivery system having an actuation assembly configured to deliver the braided implant using a reciprocating motion.

Description of Related Art

Conventional self-expanding stent delivery systems can include a handle housing portion and an elongated shaft, wherein the stent is disposed within a delivery portion at the distal end of the shaft. To deploy the stent, an outer sheath is retracted relative to the stent, whereby the stent is released from its delivery configuration. In certain systems, an inner member having a pushing mechanism disposed proximate to its distal end can be used to push the stent from the outer sheath, while the outer sheath is retracted.

However, there remains a need for a system and method for more accurately delivering an implant using a relatively simple motion and ease of use.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to systems and methods for delivering an implant. For example, an implant can be disposed within a distal end portion of an outer tubular member of the system and positioned to be engaged by a distal end portion of an inner shaft member of the system when the inner shaft member is moved distally relative to the outer tubular member. The inner shaft member can be disposed within the outer tubular member and movable distally and proximally relative to the outer tubular member. The system for delivering an implant can include a handle, a trigger, operatively coupled to the handle, and an actuation assembly operatively coupled to the trigger, the inner shaft member, and the outer tubular member.

The actuation assembly as disclosed herein is configured to displace the outer tubular member in the proximal direction a distance (d) relative to the handle and to separately move the inner shaft member distally a distance (x) relative to the handle upon deployment of the trigger from a first position to a second position, and further the actuation assembly is configured to move the inner shaft member proximally a distance (y) relative to the handle with no displacement of the outer tubular member relative to the handle upon return of the trigger from the second position to the first position.

As embodied herein, the actuation assembly can be functionally coupled to the trigger by a driving rack. The trigger can include a slide having an engagement surface to be engaged by the user. The slide can be fixedly coupled to the driving rack.

The trigger of the disclosed subject matter can be functionally connected to the driving rack by a gear train. The gear train can include a trigger gear sector, a trigger pinion operatively meshed with the trigger gear sector, a slide pinion operatively coupled to the trigger pinion, and a slid rack disposed on a slide coupled to the driving rack and operatively meshed with the trigger pinion. The driving rack can be fixedly coupled to the slide. The driving rack can be detachably coupled to the slide.

Alternatively, or additionally, the trigger can be functionally connected to the driving rack by one or more link elements. For example, a plurality of link elements can be provided. The plurality of link elements can include a first linear link coupled to the trigger at a first joint, a second linear link coupled to the slide at a second joint, and a triangle link coupled to the first linear link at a third joint and the second linear link at a fourth joint. The triangle link can be coupled to the handle at a fifth joint, and the trigger can be coupled to the handle at a sixth joint. Each of the first, second, third, fourth, fifth, and sixth joints can be pivot joints. The third joint, fourth joint, and fifth joint thus can define a triangle. Upon deployment of the trigger from the first position to the second position and return of the trigger from the second position to the first position, the third joint can trace a non-linear path. Alternatively, the trigger can be functionally connected to the driving rack by a trigger pulley system.

Furthermore, the system can include a ratchet mechanism functionally coupled to the trigger. The ratchet mechanism can include a first state configured to allow the trigger to move toward the second position and prohibit motion toward the first position. The ratchet mechanism can include a second state configured to allow the trigger to move toward the first position and prohibit motion toward the second position. As embodied herein, the ratchet mechanism can include a first pawl and a trigger ratchet rack configured to engage the pawl to permit unidirectional motion of the slide. The pawl can include a first state wherein the pawl engages the trigger ratchet rack to permit unidirectional motion of the slide in a first direction. The pawl can include a second state wherein the pawl engages the trigger ratchet rack to permit unidirectional motion of the slide in a second direction. The pawl can be configured to switch from the first state to the second state as the trigger approaches the second position from the first position. The pawl can be configured to switch from the second state to the first state as the trigger approaches the first position from the second position. The pawl can be configured to be disengaged with the trigger ratchet rack by urging the pawl away from the trigger ratchet rack. The pawl can be biased toward engagement with the trigger ratchet rack.

Additionally, the ratchet mechanism can include a second pawl having a first state wherein the second pawl engages the ratchet rack to permit unidirectional motion of the slide in a second direction. The first and second pawl can each have a second state wherein the first and second pawl do not engage the trigger ratchet rack, particularly when the other pawl is in engagement. In this manner when the first pawl is in the first state the second pawl can be in the second state and when the second pawl is in the first state the first pawl can be in the second state. The ratchet mechanism can also include a ratchet trip coupled to the first and second pawls. As the trigger approaches the second position from the first position the ratchet trip can cause the first pawl to switch from the first state to the second state and the ratchet trip can cause the second pawl to switch from the second state to the first state. As the trigger approaches the first position from the second position the ratchet trip can cause the first pawl to switch from the second state to the first state and the ratchet trip can cause the second pawl to switch from the first state to the second state.

As disclosed herein, the trigger can be coupled to a spring such that energy is stored in the spring upon deployment of the trigger from the first position to the second position, and the energy stored in the spring causes the trigger to return from the second position to the first position. The system can include a spring support coupled to the trigger and a base and configured to engage the spring such that energy is stored in the spring when the trigger is in the first position.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE FIGURES

FIGS. 5A-5D provide perspective FIG. 5A, right FIG. 5B, left FIG. 5C, and front FIG. 5D views of the trigger of the delivery system of FIG. 1.

FIGS. 8A-8D provide perspective FIG. 8A, right FIG. 8B, left FIG. 8C, and front FIG. 8D views of the slide of the delivery system of FIG. 1.

FIG. 11 provides a perspective view of the spring of the delivery system of FIG. 1.

FIGS. 12A-12C are various views depicting the spring support of the delivery system of FIG. 1.

FIGS. 13A-13D are various views depicting selected elements and the relationship between selected elements of the ratchet mechanism of the delivery system of FIG. 1.

FIGS. 17A-17D provide various views of selected elements and the relationship between selected elements of the ratchet mechanism of the delivery system of FIG. 14.

DETAILED DESCRIPTION

Figure 1:
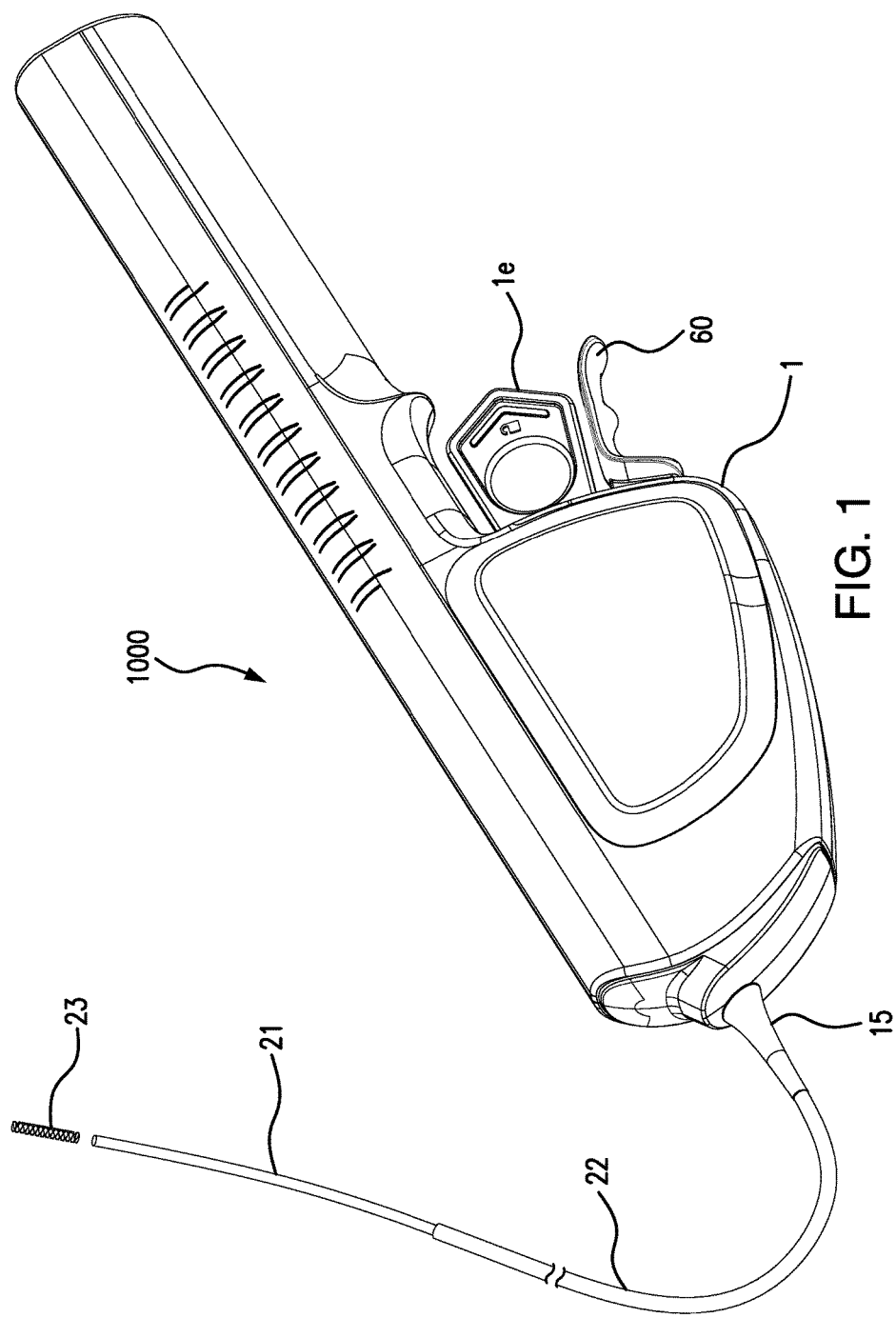
FIG. 1 is a perspective view of an exemplary embodiment of a delivery system in accordance with the disclosed subject matter.

Reference will now be made in detail to the various exemplary embodiments of the disclosed subject matter, exemplary embodiments of which are illustrated in the accompanying drawings. The structure and corresponding method of making and using the disclosed subject matter will be described in conjunction with the detailed description of the delivery system. The methods and systems described herein can be used for delivering a medical device, such as a stent, scaffold stent graft, valve, filter, or other suitable implant to a desired location in a patient.

Generally, and as set forth in greater detail, the disclosure subject matter provided herein includes a delivery system having a handle, a trigger, and an actuation assembly. The trigger is operatively coupled to the handle. The actuation assembly is operatively coupled to the trigger, the inner shaft member, and the outer tubular member. As used herein the terms "functionally" and "operatively" as used with "coupled," "engaged," or "connected," are interchangeable and understood by one of skill in the art. The actuation assembly is configured to displace the outer tubular member in the proximal direction a distance (d) relative to the handle and to separately move the inner shaft member distally a distance (x) relative to the handle upon deployment of the trigger from a first position to a second position, and further wherein the actuation assembly is configured to move the inner shaft member proximally a distance (y) relative to the handle with no displacement of the outer tubular member relative to the handle upon return of the trigger from the second position to the first position.

In accordance with the described subject matter, a trigger assembly for a delivery system is also provided. The trigger assembly includes a trigger functionally connected to the actuation assembly by a driving rack, a gear train functionally disposed between the trigger and the driving rack. The gear train includes a trigger gear sector, a trigger pinion operatively meshed with the trigger gear sector, a slide pinion operatively coupled to the trigger pinion, and a slide rack disposed on a slide coupled to the driving rack and operatively meshed with the trigger pinion.

A variety of types of medical devices are suitable for delivery by the delivery system of the present invention. For purpose of illustration and not limitation, the delivery system is described herein with a medical device depicted as a self-expanding stent. Particularly, although not by limitation, reference is made herein to the implant being a braided stent or scaffold for purpose of illustration only. However, the delivery system presently disclosed is not limited to the delivery of self-expanding stents. Other devices can also be used. For example, scaffolds, coils, filters, stent grafts, embolic protection devices, and artificial valves can be delivered within a patient's vasculature, heart, or other organs and body lumens using the disclosed delivery system. Other devices such as a prosthesis retrieval mechanism can also be delivered with the delivery system to a predetermined location in a patient's luminal system. Moreover, a combination of medical devices and/or beneficial agents can also be delivered using the disclosed subject matter. For example, multiple stents and/or a combination of stents and embolic protection devices and/or beneficial agents can be delivered by the disclosed subject matter, as described below. Additional information related to delivery of implants can be found in U.S. application Ser. No. 11/876,764, filed on Oct. 22, 2007, and U.S. application Ser. No. 13/118,325, filed on May 27, 2011, each of which is incorporated by reference in its entirety herein.

Figure 3:
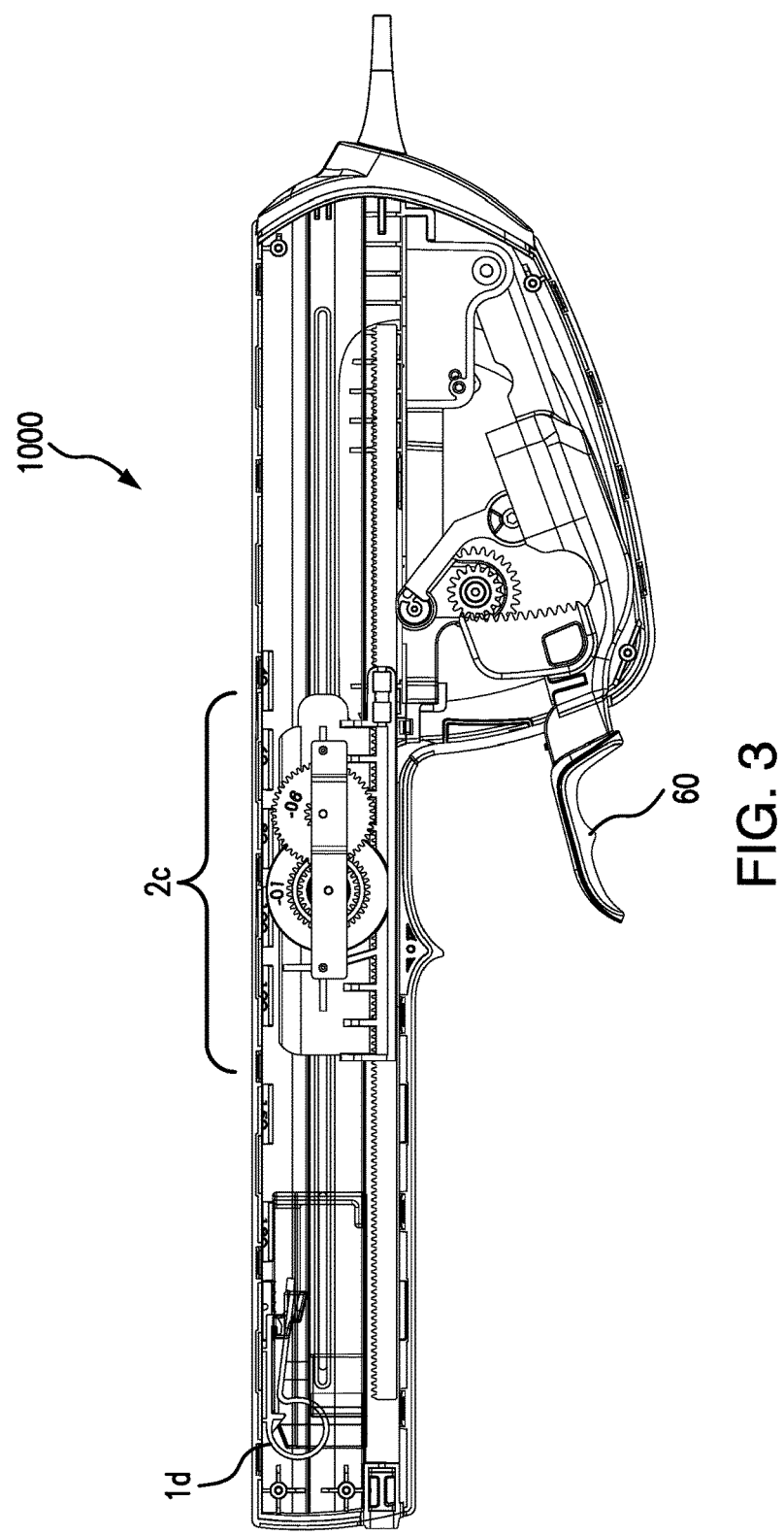
FIG. 3 is a left side view, with a portion of the handle housing removed, of the delivery system of FIG. 1.

Referring to FIG. 1 for the purpose of illustration and not limitation, various embodiments of the delivery systems disclosed herein generally can include a handle 1, an outer tubular member 22, and an inner shaft member 21. An implant 23, for example, a braided implant can be provided with the system or independently. The handle can include a trigger assembly including a trigger 60 movable between and first position and a second position, and an actuation assembly 2 (see e.g., FIG. 3) operatively coupled to the trigger 60. The outer tubular member 22 can include a proximal end portion and a distal end portion. The outer tubular member 22 can be operatively coupled to the actuation assembly 2 and can be movable in a proximal direction relative to the handle 1. A stabilizer tube (not shown) can be disposed over at least the proximal end portion of the outer tubular member 22, and a strain relief 15 can be used to couple the stabilizer tube and the handle 1. The inner shaft member 21 can include a proximal end portion and a distal end portion. The inner shaft member 21 can be disposed within the outer tubular member 22 and can be operatively coupled to the actuation assembly 2. The inner shaft member 21 of the disclosed delivery system is movable distally and proximally relative to the outer tubular member 22. The implant 23 can be disposed within the distal end portion of the outer tubular member 22 and can be positioned to be engaged by the distal end portion of the inner shaft member 21 when the inner shaft member is moved distally relative to the outer tubular member 22. The distal end portion of the inner shaft member 21 can have a pushing mechanism disposed thereon. For example, U.S. application Ser. No. 13/118,325, filed on May 27, 2011, which is incorporated by reference in its entirety herein, discloses suitable pusher elements for the delivery system. The outer tubular member 22 is depicted with a break in FIG. 1 to indicate that the length shown is only exemplary and the outer tubular member 22 and inner shaft member 21 can be longer than shown. Indeed, any suitable length can be used. As an example and not by way of limitation, the outer tubular member 22 and inner shaft member 21 can be long enough to extend from outside the body of a patient through a tortuous path to a treatment location within the body of a patient. The handle 1 can further include a luer lock at the proximal end of the handle to receive a guidewire therethrough which can extend through the inner shaft member and/or a flushing device as desired.

The actuation assembly 2 of the disclosed subject matter is configured to displace the outer tubular member 22 in the proximal direction a distance (d) relative to the handle 1 and to separately move the inner shaft member 21 distally a distance (x) relative to the handle 1 upon deployment of the trigger 60 from the first position to the second position. Furthermore, the actuation assembly 2 is configured to move the inner shaft member 21 proximally a distance (y) relative to the handle 1 with no displacement of the outer tubular member 22 relative to the handle 1 upon return of the trigger 60 from the second position to the first position. Put another way, the actuation assembly 2 can be configured to move the outer tubular member 22 in a proximal direction relative to the handle 1 and to separately move the inner shaft member 21 distally relative to the outer tubular member 22 upon deployment of the trigger 60 form the first position to the second position. The actuation assembly 2 can further be configured to move the inner shaft member 21 proximally relative to the outer tubular member 22 with no displacement of the outer tubular member 22 relative to the handle 1 upon return of the trigger 60 from the second position to the first position. Repeatedly deploying the trigger 60 from the first position to the second position and returning the trigger from the second position to the first position can cause the inner shaft member 21 to urge the implant 23 from the outer tubular member 22.

The distance (y) minus the distance (x) can be substantially equal to the distance (d). Upon deployment of the trigger 60 from the first position to the second position and return of the trigger 60 from the second position to the first position a net displacement of the inner shaft member 21 relative to the outer tubular member 22 thus can be zero. The implant 23 can have a length, and the length of the implant 23 can be less than the distance (x). Example lengths of the implant 23, for purpose of illustration and not limitation, can be 20 mm, 30 mm, 40 mm, 60 mm, 80 mm, 100 mm, 120 mm, and 150 mm.

The distances (d), (x) and (y) can be selected based at least in part on the diameter of the implant to be delivered, the desired compression of the implant to be delivered, the path between the insertion point and the location of implant delivery, and/or other variables. As an example, and not by way of limitation, for a stent having a diameter of 4.5 mm when delivered to the vasculature, (d) can be about 12 mm, (x) can be about 28 mm, and (y) can be about 40 mm. As another example and not by way of limitation, the ratio (referred to herein as the "gear ratio") between the net distal motion of the inner shaft member 21 relative to the outer shaft member 22 (i.e., the distance (d) plus the distance (x)) to the distance (d) can be greater than 3. As an example, the gear ratio of (12+28):(12) is about 3.3. The actuation assembly disclosed herein having such a gear ratio can be used to properly deploy a braided stent from an extended delivery configuration to an expanded deployed configuration and address a 3:1 change in length of the stent from the delivery length to the deployment length. Exemplary diameters for stents when delivered to the vasculature can range from 4 mm to 12 mm or greater, such as, exemplary diameters can be 4.5 mm, 5.0 mm, 5.5 mm, 6.0 mm, 6.5 mm, 7.5 mm, or 8 mm, or suitable increments therebetween.

With regard to the trigger assembly, and for the purpose of illustration, and not limitation, an exemplary embodiment of a system for delivering an implant is shown in FIG. 1 and is designated generally by reference character 1000. Portions of this exemplary embodiment are depicted in FIGS. 2-13. The handle 1 can include a first handle housing portion 1a and a second handle housing portion 1b. The system can also include a trigger 60. The trigger 60 is operatively coupled to the handle and moveable between a first position and a second position. Furthermore the trigger can be biased towards the first and/or second position, for example, by a spring 91 (FIG. 11). As described in further detail below, the trigger assembly can further include a ratchet mechanism 80 which can prevent moving the trigger between the first and second positions. Particularly, the ratchet can be configured to require a full stroke of the trigger in one direction to allow motion of the trigger in the opposite direction. Additionally, the trigger can include a trigger stop 67. The trigger stop 67 can be disposed between the trigger 60 and the handle 1, and can limit how far the trigger 60 can be actuated. The size of trigger stop 67 can be selected based at least in part on the diameter of the stent to be delivered, the desired compression of the stent to be delivered, the path between the insertion point and the location of stent delivery, and/or other variables. The system 1000 can also include an actuation assembly 2. A variety of suitable actuation assemblies that can be used in conjunction with the trigger assembly disclosed herein are disclosed in U.S. patent application Ser. No. 14/932,848; U.S. patent application Ser. No. 14/932,875; U.S. patent application Ser. No. 14/932,862; U.S. patent application Ser. No. 14/932,884, filed concurrently herewith, or otherwise known in the art. The actuation assembly 2 can be operatively coupled to the trigger 60, the inner shaft member 21 and the outer tubular member 22.

Figure 2:
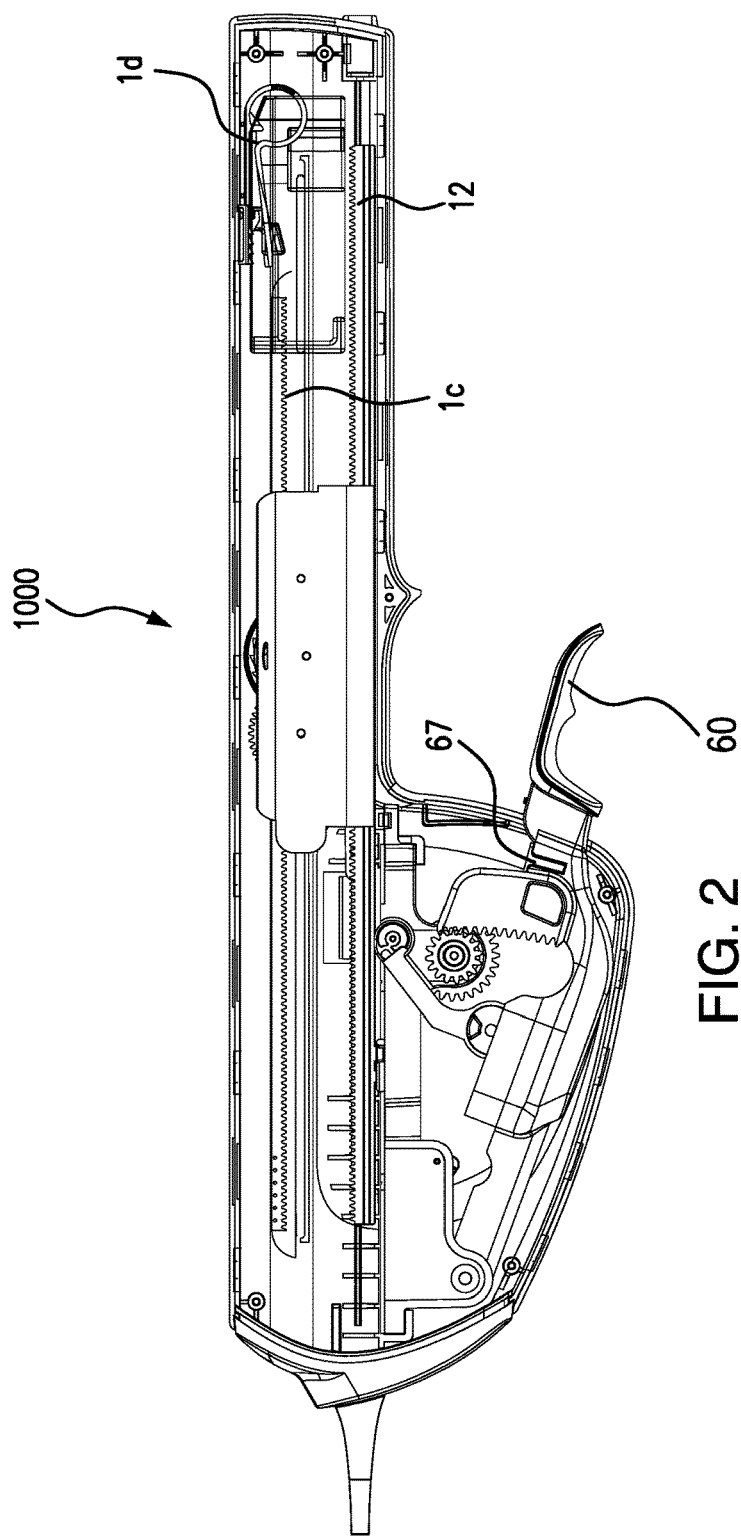
FIG. 2 is a right side view, with a portion of the handle housing removed, of the delivery system of FIG. 1.

As embodied herein, and with reference to FIG. 2, the trigger 60 can be coupled to the actuation assembly 2 by a driving rack 12. For example, the trigger 60 can be functionally coupled to the driving rack by gear train. The gear train can include a trigger gear sector 63 (FIG. 5), a trigger pinion 64 (FIG. 6), a slide pinion 65 (FIG. 7), a slide 61 (FIG. 8; sometimes referred to as an intermediate element) having a slide rack 66, and a base 81 that can support certain elements of the gear train (FIG. 9). The trigger 63 can be pivotally coupled to the base 81. The trigger gear sector 63 can be coupled to the trigger 60, for example, the trigger gear sector 63 can be unitary with the trigger 60, and can be operatively meshed with the trigger pinion 64. The trigger pinion 64 can be operatively coupled to the slide pinion 65. For example, the trigger pinion 64 and the slide pinion 65 can be coupled by splines and grooves, such as, four splines on the trigger pinion 64 configured to be received by four grooves in the slide pinion 65 as depicted in FIGS. 6 and 7. The slide pinion 65 can be operatively meshed with the slide rack 66 disposed on the slide 61. The driving rack 12 can be coupled to the slide 61. The driving rack 12 can be fixedly coupled or releasably coupled to the slide 61. As an example and not by way of limitation, the driving rack 12 can have a bayonet-type engagement with the slide 61. Furthermore, more than one trigger gear sector and/or trigger pinion can be provided, as shown, for example, in FIGS. 1-4 and 9, the gear train can include two trigger gear sectors 63 and two trigger pinions 64. Each of the trigger pinions 64 can be coupled to the slide pinion 65 as described above.

As embodied herein, the slide pinion 65 can be quad symmetrical. For example, the slide pinion 65 can have 28 teeth evenly distributed in sets of 7. The number of grooves can be a factor of the number of teeth, for example, 4 grooves and 28 teeth. Such a configuration can allow for symmetry between the teeth and the grooves of the slide pinion 65, and thus ease of assembly and/or use. Accordingly, when the slide pinion 65 is coupled the trigger pinion 64, the teeth are in proper alignment. Additionally or alternatively, the slide pinion 65 can include teeth around only a portion of the circumference. For example, rather than including teeth about the entire circumference, a number of teeth (e.g., 10 teeth) can be removed or omitted. This arrangement can accommodate other elements, for example, the movement of spring 90 (described in greater detail below) toward the slide pinion 65 during movement of the trigger 60 when space is restricted. Furthermore, at least one spline can be configured to align radially a selected location, e.g., a missing tooth, so as to allow for self-alignment.

Figure 4:
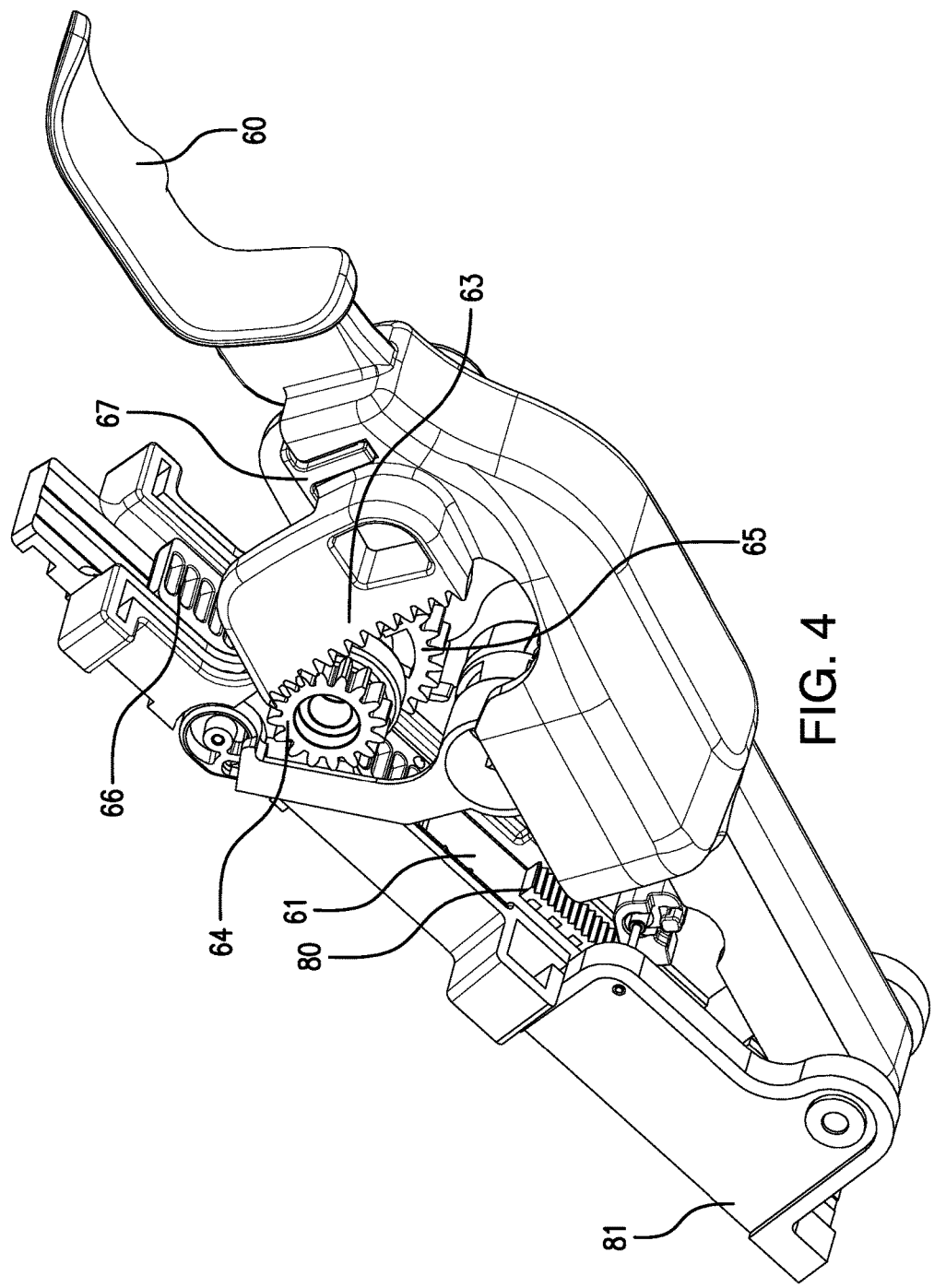
FIG. 4 provides a top perspective view of selected elements of the trigger assembly of the delivery system of FIG. 1.
Figure 6D:
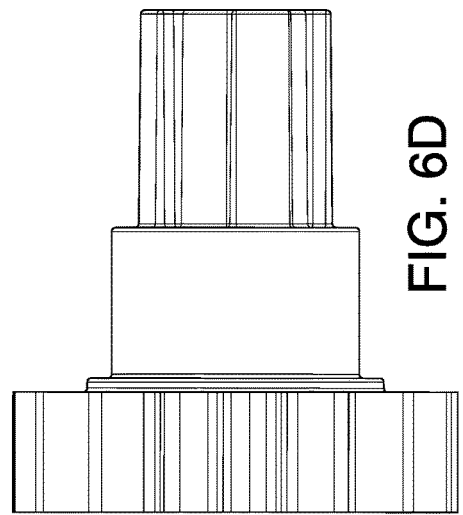
FIGS. 6A-6D provide perspective FIG. 6A, right FIG. 6B, left FIG. 6C, and front FIG. 6D views of the trigger pinion of the delivery system of FIG. 1.
Figure 6B:
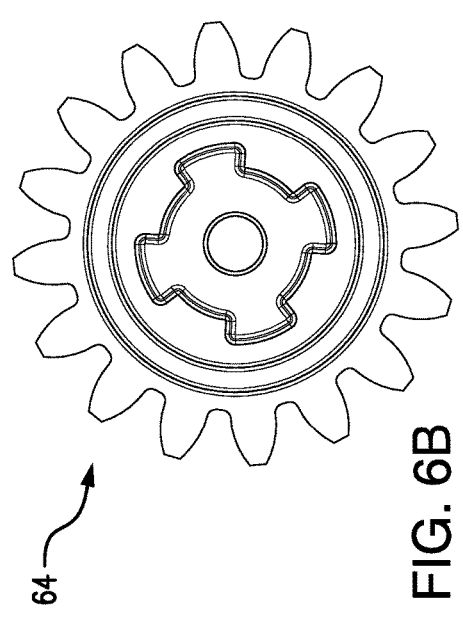
Figure 6A:
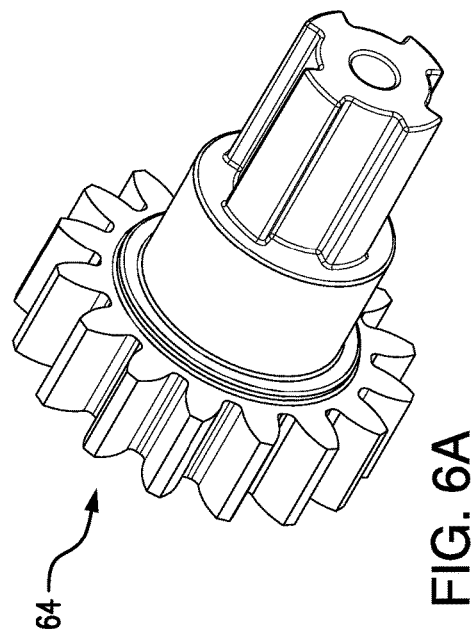
Figure 6C:
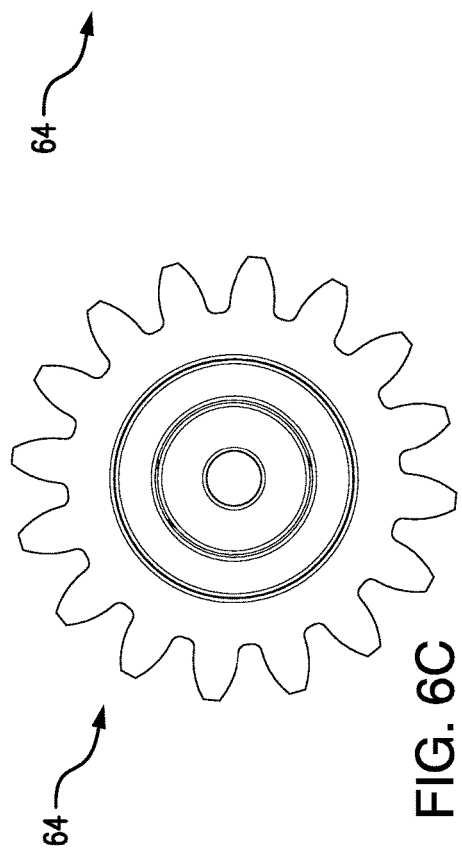
Figure 7A:
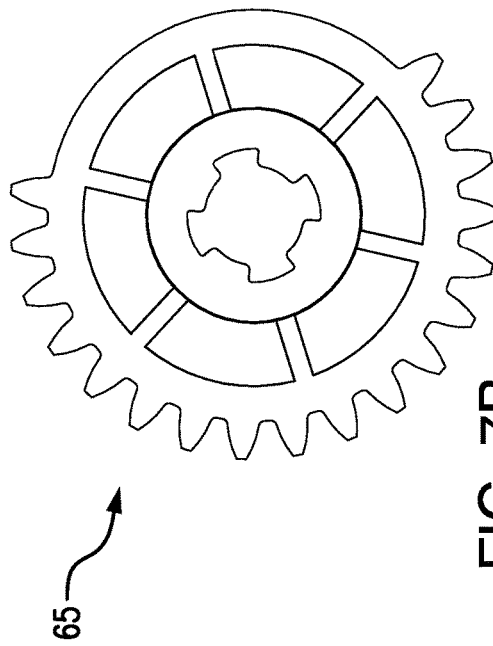
FIGS. 7A-7D provide perspective FIG. 7A, right FIG. 7B, left FIG. 7C, and front FIG. 7D views of the slide pinion of the delivery system of FIG. 1.
Figure 7B:
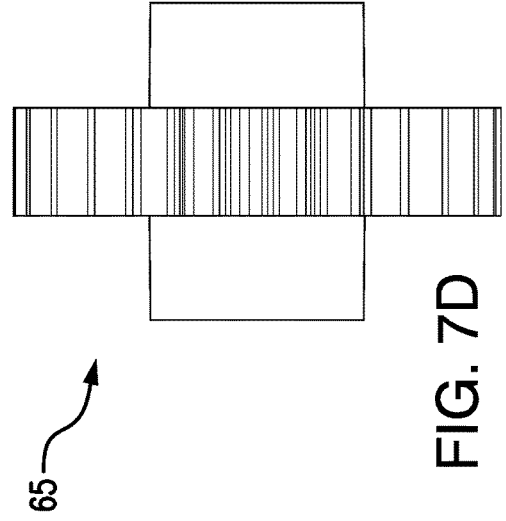
Figure 7C:
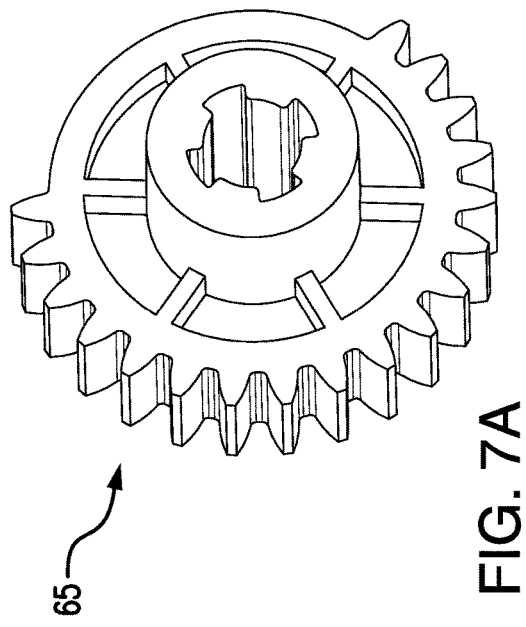
Figure 7D:
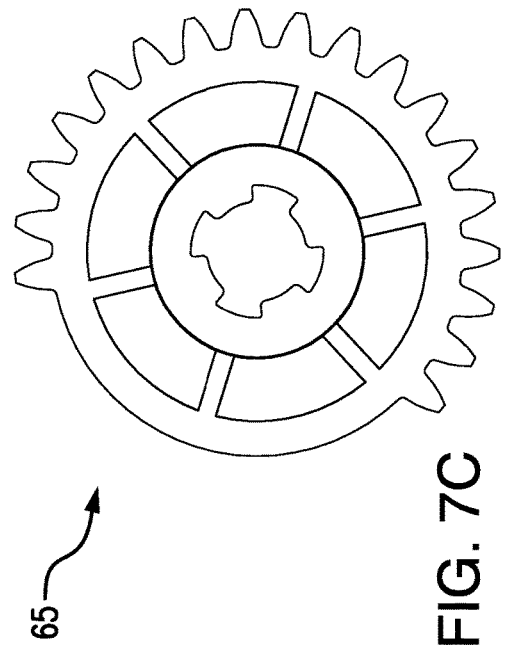
Figure 9A:
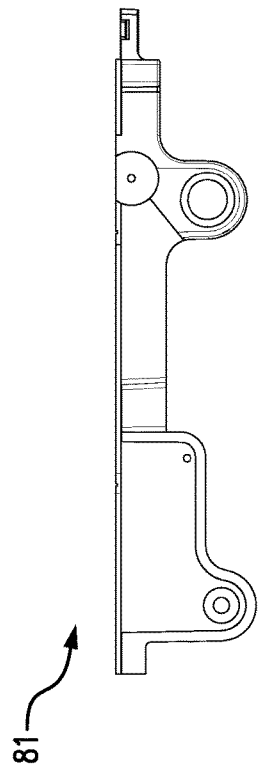
FIGS. 9A-9D provide perspective FIG. 9A, right FIG. 9B, left FIG. 9C, and front FIG. 9D views of the base of the delivery system of FIG. 1.
Figure 9B:
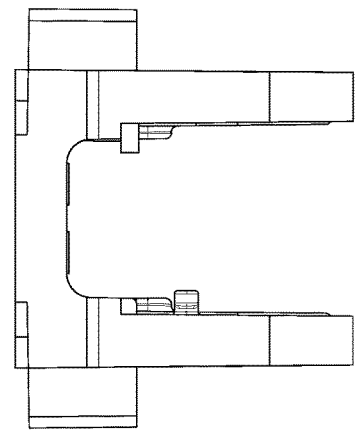
Figure 9C:
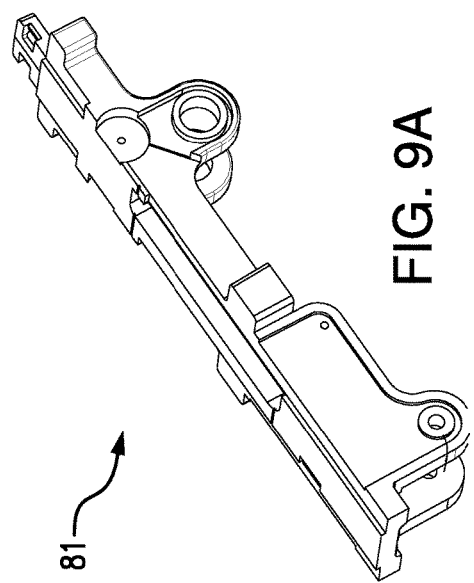
Figure 9D:
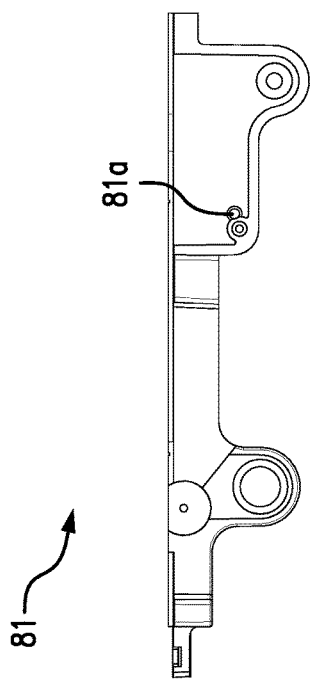
Figure 10:
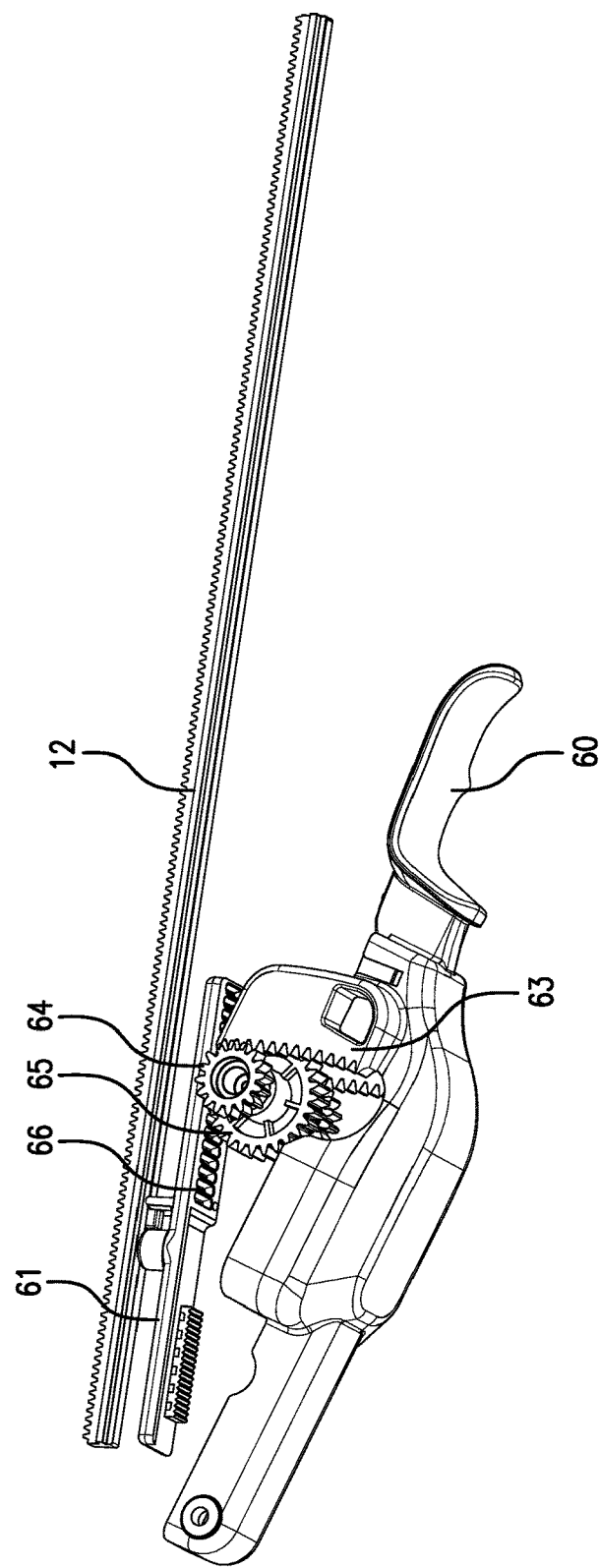
FIG. 10 is a perspective view illustrating the relationship between selected elements of the delivery system of FIG. 1.

With reference to FIGS. 11 and 12, for the purpose of illustration and limitation, a spring 90 can be provided. The spring can be, for example, a torsion spring 90. Additional springs can likewise be provided, e.g., two springs 90, as depicted in FIG. 4. The spring 90 can be coupled to the trigger such that energy is stored in the spring 90 upon deployment of the trigger 60 from the first position to the second position. The energy stored in the spring 90 thus can be configured to bias the trigger 60 to return from the second position to the first position. The spring 90 can be housed within a spring support 91 (FIG. 12). The spring support can be coupled to the trigger 60 and the base 81. The spring support 91 can house the spring 90 such that energy is stored in the spring 90 when the trigger 60 is in the first position, e.g., the spring support 91 can hold the spring 90 in a pre-loaded position. Such a configuration can cause a force to be felt as the user initially begins to move the trigger 60 from the first position to the second position. Additionally, by providing such a configuration, the spring can provide additional force or bias to assist in returning the trigger 60 from the second position to the first position, and thus ensure that the trigger 60 returns from the second position to the first position.

The spring support 90 can be configured to house and/or strengthen the spring, such as an exoskeleton arrangement. For example, the spring support 90 can have legs configured to engage the legs of the torsion spring 90, as depicted in FIG. 12. The legs of the spring support 91 can be configured to move with the legs of the torsion spring 90. If the spring includes a barrel portion, the spring support 91 can also include a barrel portion to accommodate the barrel portion of the spring 90. The spring support 91 can be a single piece element, or can include several elements coupled together to form the spring support (FIG. 12C). The elements when assembled thus can be configured to allow the spring support to move with the spring 90, but prevent the spring from fully relaxing. The spring support 91 thus can reduce or prevent loads on other elements of the delivery system, for example, the trigger 60 and the base 81, which can be plastic. That is, the spring support 91 can be made from metal or other suitably strong materials, preferably such materials that are not susceptible to creep under stress.

In accordance with another aspect of the disclosed subject matter, the delivery system can include a ratchet mechanism. With reference to FIG. 13, for the purpose of illustration and not limitation, the system can include ratchet mechanism 80. The ratchet mechanism 80 can include a first state and a second state. The first state can be configured to allow the trigger 60 to move toward the second position and prohibit motion toward the first position. The second state can be configured to allow the trigger 60 to move toward the first position and prohibit motion toward the second position. Such a system thus can be configured to require the user to perform a full stroke of the trigger 60 between the first and second position before allowing return movement in the opposite direction.

The ratchet mechanism 80 can include a first pawl 82. The first pawl 82 can be supported by a peg 86 coupled to the base 81. The first pawl 82 can pivot relative the peg, and thus relative the base 81. The first pawl 82 can also be coupled to one end of a ratchet spring 87 (not shown for purpose of clarity), which can be coupled to the base 81 at its opposite end. The ratchet mechanism 80 also can include a trigger ratchet rack 83 and the like. The trigger ratchet rack 83 can be disposed on the slide 61. The trigger ratchet rack 83 can be configured to engage the first pawl 82 to permit unidirectional motion of the slide 61. By limiting the slide 61 to unidirectional motion, the trigger can likewise be limited to unidirectional motion (i.e., toward the first state or toward the second state). The first pawl 82 can have a first state configured to allow the trigger 60 to move toward the second position and prohibit motion toward the first position and a second state configured to allow the trigger 60 to move toward the first position and prohibit motion toward the second position. The ratchet spring 87 can keep the pawl 82 biased toward the first position or the second position, selectively. That is, the pawl 82 can be configured to switch from the first state to the second state as the trigger approaches the second position from the first position. Likewise, the pawl 82 can be configured to switch from the second state to the first state as the trigger approaches the first position from the second position. For example and not by way of limitation, the trigger ratchet rack 83 can be configured to move past the first pawl 83, as the trigger approaches either the first position or the second position, respectively, and thus allow the first pawl 82 to move freely to the alternate state due to the bias of ratchet spring 87. As described herein, the pawl 83 can engage the ratchet rack 83 in both the first position and the second position. Additionally or alternatively, the ratchet mechanism can be configured with more than one rack, for example a dual rack, and the pawl 83 can engage a different rack in each state. The pawl 82 can be moved out of the first or second position to a third position (e.g., a defeated position) in which the pawl 82 does not engage the trigger ratchet rack 83. As an example, the pawl 82 can be moved to the defeated position by moving the pawl 83 perpendicular to the trigger ratchet rack 83 along peg 86. The base 81 can include a defeat hole 81a (FIG. 9c), which can be aligned with the pawl 82 and can be aligned with a similar defeat hole in the handle 1, such that the pawl 82 can be defeated by pushing an instrument through the defeat holes and urging the pawl 82 along the peg 86. Peg 86 can be configured to prevent the pawl 82 from returning to the first or second positions once the pawl has been moved to the defeated position. For example and as shown in FIG. 13d, the peg 86 can have a variable diameter. The pawl 82 can be disposed on the larger diameter in the first or second position, and can be disposed on the smaller diameter in the defeated position. Furthermore, a damper can be disposed on the pawl 82, for example rubber, for reduced noise. The ratchet spring 87 can also be dampened.

For purpose of illustration, reference is now made to the operation of the system with the actuation assembly disclosed herein. In operation, the user can deploy the trigger 60 from the first position to the second position (referred to herein as the "first action"). The trigger can cause movement of the trigger gear sector 63. The trigger gear sector 63 can be functionally meshed with the trigger pinion 64 and can cause rotation of the trigger pinion 64. The trigger pinion 64 can be operatively coupled to the slide pinion 65, and can cause rotation of the slide pinion 65. The slide pinion 65 can be functionally engaged with the slide rack 66 and can cause the slide rack 66 to move distally. The slide rack 66 can be coupled to the driving rack 12, and the driving rack 12 can also move distally. The driving rack 12 can be functionally coupled to the actuation assembly, and can cause the inner shaft member 21 to move distally relative to the handle, and the outer tubular member to move proximally relative to the handle. Thus, during the first action, the inner shaft member 21 can move distally relative to the handle 1 and the outer tubular member 22 can move proximally relative to the handle 1. During the first action, the pawl 82 can be in the first state and can be configured to allow the trigger 60 to move toward the second position and prohibit motion toward the first position. The pawl 82 can be configured to switch from the first state to the second state as the trigger approaches the second position from the first position.

Upon return of the trigger 60 from the second position to the first position (herein referred to as the "second action"), which can be caused, for example, by the energy stored in the spring 90, the trigger can cause movement of the trigger gear sector 63 in the opposition direction as the first action. The trigger gear sector 63 can cause rotation of the trigger pinion 64. The trigger pinion 64 can cause rotation of the slide pinion 65. The slide pinion 65 can cause the slide rack 66 to move proximally. The driving rack 12 can be functionally coupled to the actuation assembly, and can cause the inner shaft member 21 to move proximally relative to the handle, and the outer tubular member 22 remain stationary relative to the handle. Thus, during the second action, the inner shaft member 21 moves proximally relative to the handle 1 and the outer tubular member 22 is stationary relative to the handle. During the second action, the pawl 82 can be in the second state and can be configured to allow the trigger 60 to move toward the first position and prohibit motion toward the second position. The pawl 82 can be configured to switch from the second state to the first state as the trigger approaches the first position from the second position.

Figure 14:
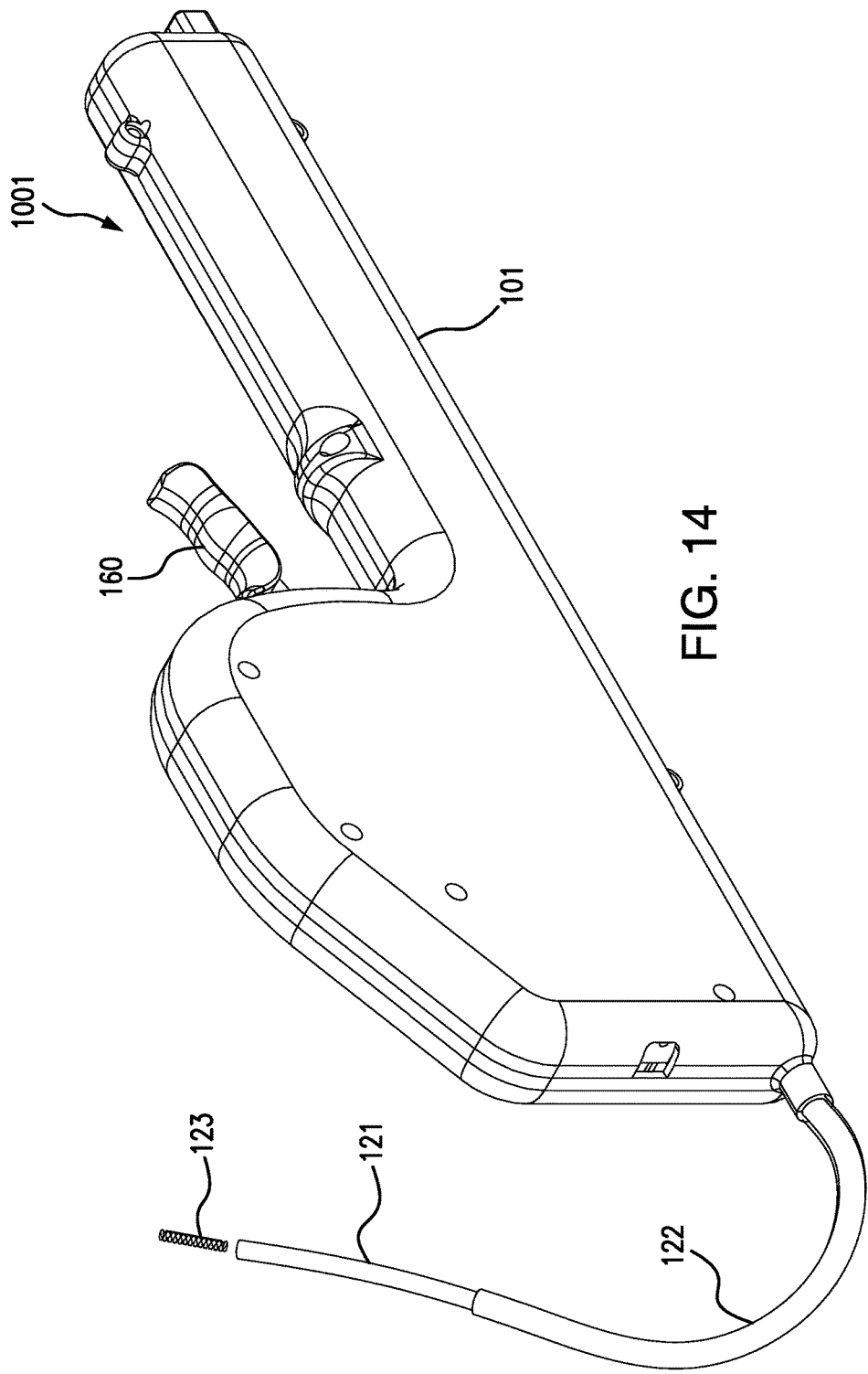
FIG. 14 is a perspective view of another exemplary embodiment of a delivery system in accordance with the disclosed subject matter.
Figure 15:
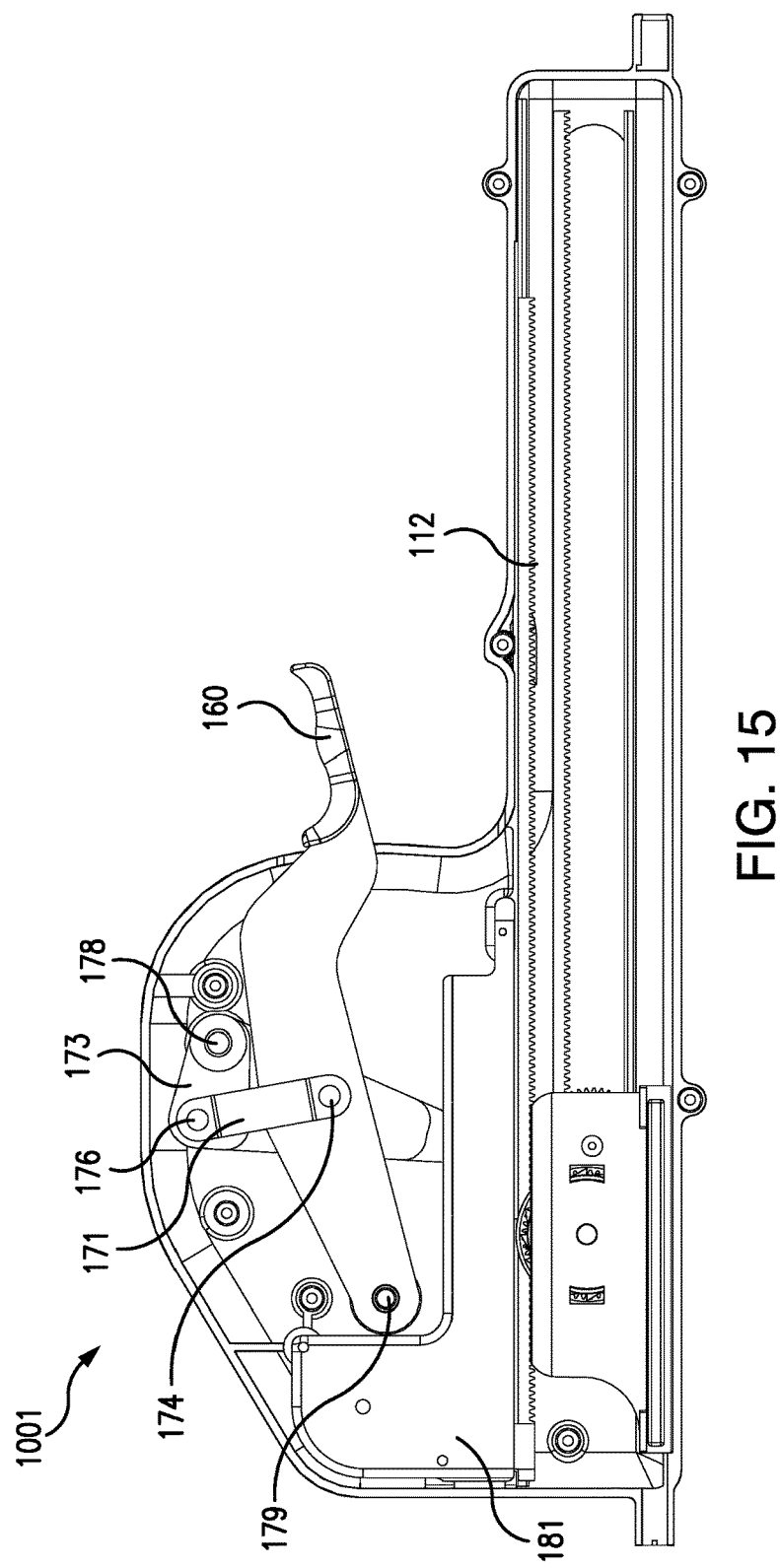
FIG. 15 is a right side view, with a portion of the handle housing removed, of the delivery system of FIG. 14.
Figure 16:
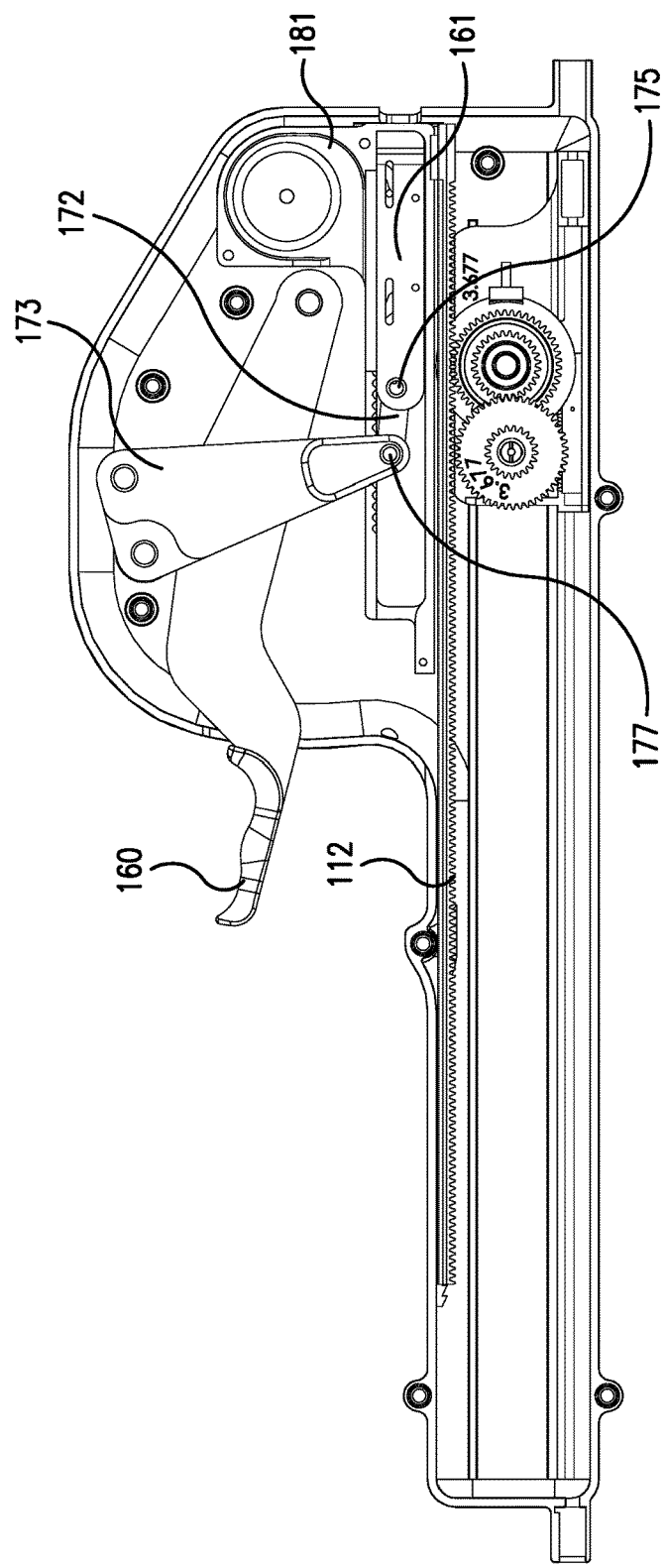
FIG. 16 is a left side view, with a portion of the handle housing removed, of the delivery system of FIG. 14.

In accordance with an alternative embodiment of the disclosed subject matter, a delivery system is provided wherein the trigger is coupled to the driving rack by a plurality of link elements. Referring now to FIG. 14 for the purpose of illustration and not limitation, an exemplary embodiment of a system for delivering an implant is provided and designated generally by reference character 1001. Portions of this exemplary embodiment are depicted in FIGS. 15-17. Elements that are similar to the previously described embodiment have been given like numbers. The delivery system 1001 can be configured to deliver an implant in a similar manner as described herein above.

The delivery system 1001 can include a handle 101, an outer tubular member 122, an inner shaft member 121, and an implant 123, for example, a braided implant. The handle 101 can include a trigger 160 and an actuation assembly 102, which can be configured to move the inner shaft member 121 and the outer tubular member 122 relative to the handle 101 as described above upon deployment of the trigger 160 from the first position to the second position and return from the second position to the first position. The trigger 160 can include a lock as described herein above.

With reference to the exemplary embodiment herein, the trigger 160 can be coupled to the driving rack 112 by a plurality of link elements. The link elements can include a first and second linear links 171 and 172, a triangle link 173, and a slide 161. A base 181 can support the slide 161 and can have a trigger ratchet rack 183 disposed thereon. The first linear link 171 can be coupled to the trigger 160 at a first joint 174. The second linear link can be coupled to the slide 161 at a second joint 175. The triangle link 173 can be coupled to the first linear link 171 at a third joint 176 and the second linear link 172 at a fourth joint 177. The triangle link 173 can be coupled to the handle at a fifth joint 178 and the trigger 160 can be coupled to the handle at a sixth joint 179. Each of the first, second, third, fourth, fifth, and sixth joints (174-179) can be pivot joints. The third joint 176, fourth joint 177, and fifth joint 178 can define a triangle. The slide 161 can be coupled to the driving rack 112. The driving rack 112 can be fixedly coupled or releasably coupled to the slide 161. As an example and not by way of limitation, the driving rack 112 can have a bayonet-type engagement with the slide 161 (sometimes referred to herein as an intermediate element). A spring (not shown), such as a constant force spring or tape measure spring, can be coupled to the slide 161 and configured to bias the trigger 160 toward the first position. The spring can be supported in base 181. In particular embodiments, the spring can be coupled to any suitable link of the plurality of links to bias the trigger 160 toward the first position.

With reference to FIG. 17, for the purpose of illustration and not limitation, the system can also include a ratchet mechanism 180. The ratchet mechanism 180 can include a first state and a second state. The first state can be configured to allow the trigger 160 to move toward the second position and prohibit motion toward the first position. The second state can be configured to allow the trigger 160 to move toward the first position and prohibit motion toward the second position. Such a system can be configured to require the user to perform a full stroke of the trigger 160 between the first and second position, such as described above.

As embodied herein, for illustration and not limitation, the ratchet mechanism 180 can include a first pawl 182 as well as a second pawl 184. The first and second pawls 182 and 184 can be supported on the slide 161 and can include a ratchet trip 185 disposed between the first and second pawls 182 and 184. The first and second pawls 182 and 184 can each have a first state in which the pawls engage the trigger ratchet rack 183 to permit unidirectional motion of the slide. The first pawl 182 can allow motion in a first direction and the second pawl 182 can allow motion in a second direction. The first and second pawls 182 and 184 can each have a second state wherein the first and second pawls 182 and 184 do not engage the trigger ratchet rack 183. That is, when the first pawl 182 is in the first state the second pawl 184 can be in the second state, and when the second pawl 184 is in the first state the first pawl 182 can be in the second state. As the trigger 160 approaches the second position from the first position, the ratchet trip 185 can cause the first pawl 182 to switch (or disengage) to from the first state to the second state and the ratchet trip 185 can cause the second pawl 184 to switch (or engage) from the second state to the first state. Likewise, as the trigger 160 approaches the first position from the second position, the ratchet trip 185 can cause the first pawl 182 to switch (or engage) from the second state to the first state and the ratchet trip 185 can cause the second pawl 184 to switch (or disengage) from the first state to the second state. The system can be configured to ensure that the pawls are not simultaneous in the first state. The first pawl 182 and the second pawl 184 can each be in the second position at the same time to defeat the ratchet mechanism 180. Furthermore, the pawls and springs can be damped as described hereinabove.

In operation of this exemplary embodiment, the user can deploy the trigger 160 from the first position to the second position (referred to herein as the "first action"). The trigger 160 can pivot at the sixth joint 179 (clockwise in FIG. 15). The trigger 160 can pull on the first linear link 171, which can cause the triangle link 173 to pivot at fifth joint 178 (counter clockwise in FIG. 15). The triangle link 173 can pull second linear link 172 proximally, which can pull slide 161, and therefore driving rack 112, proximally. The driving rack 112 can be functionally coupled to the actuation assembly, and can cause the inner shaft member 121 to move distally relative to the handle, and the outer tubular member 222 to move proximally relative to the handle. Thus, during the first action, the inner shaft member 121 can move distally relative to the handle 101 and the outer tubular member 122 can move proximally relative to the handle 101. During the first action, the first pawl 182 can be in the first state and can be configured to allow the trigger 160 to move toward the second position and prohibit motion toward the first position. The second pawl 184 can be in the second position, and thus not engaged with the trigger ratchet rack 183. First and second pawls 182 and 184 can be configured to switch from the first state to the second state and from the second state to the first state, respectively, as the trigger approaches the second position from the first position. The transition of each pawl can be timed such that each pawl 182 and 184 is in the second state for a period of time before the second pawl 184 switches to the first state.

Upon return of the trigger 160 from the second position to the first position (herein referred to as the "second action"), which can be caused, for example, by the energy stored in the spring 190, the trigger 160 can pivot at the sixth joint 179 (counter clockwise in FIG. 15). The trigger can push on the first linear link 171, which can cause the triangle link 173 to pivot at fifth joint 178 (clockwise in FIG. 15). The triangle link 173 can push the second linear link 172 distally, which can push slide 161, and therefore driving rack 112, distally. The driving rack 112 can be functionally coupled to the actuation assembly, and can cause the inner shaft member 121 to move proximally relative to the handle, and the outer tubular member 122 remain stationary relative to the handle. Thus, during the second action, the inner shaft member 121 moves proximally relative to the handle 101 and the outer tubular member 122 is stationary relative to the handle. During the second action, the second pawl 184 can be in the first state and can be configured to allow the trigger 160 to move toward the first position and prohibit motion toward the second position. The first pawl 182 can be in the second position and thus not engaged with the trigger ratchet rack 183. First and second pawls 182 and 184 thus can be configured to switch from the second state to the first state and from the first state to the second state, respectively, as the trigger approaches the first position from the second position. Additionally or alternatively, the transition of each pawl can be timed such that each pawl 182 and 184 is in the second state for a desired period of time before the first pawl 182 switches to the first state.

As embodied herein, upon deployment of the trigger 160 from the first position to the second position and return of the trigger 160 from the second position to the first position, the third joint 176 can trace a non-linear path. Such non-linear motion can result in a variable force required to move the trigger 160 between positions along the path of the trigger 160.

Figure 18:
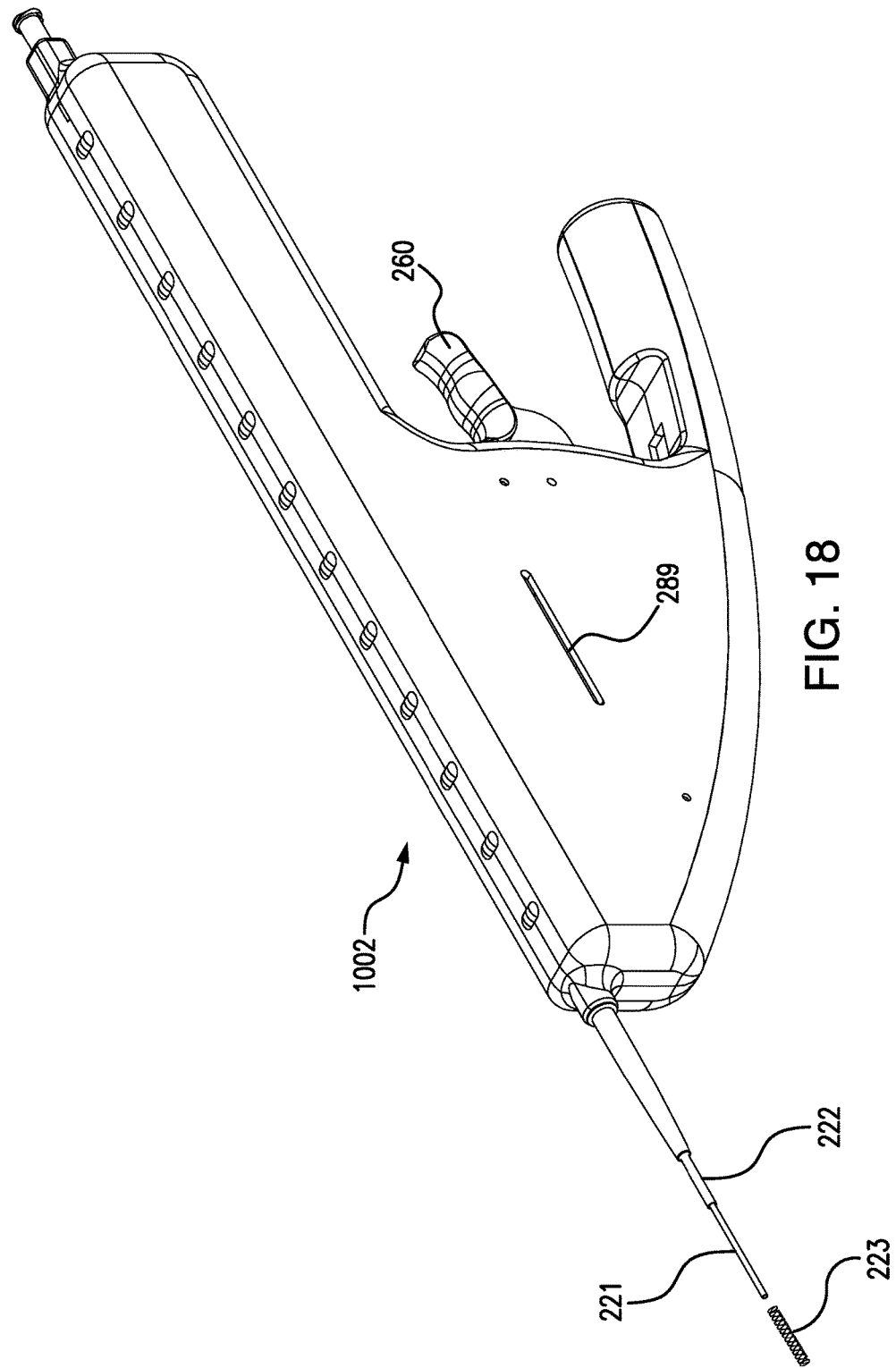
FIG. 18 is a perspective view of yet another exemplary embodiment of a delivery system in accordance with the disclosed subject matter.
Figure 19:
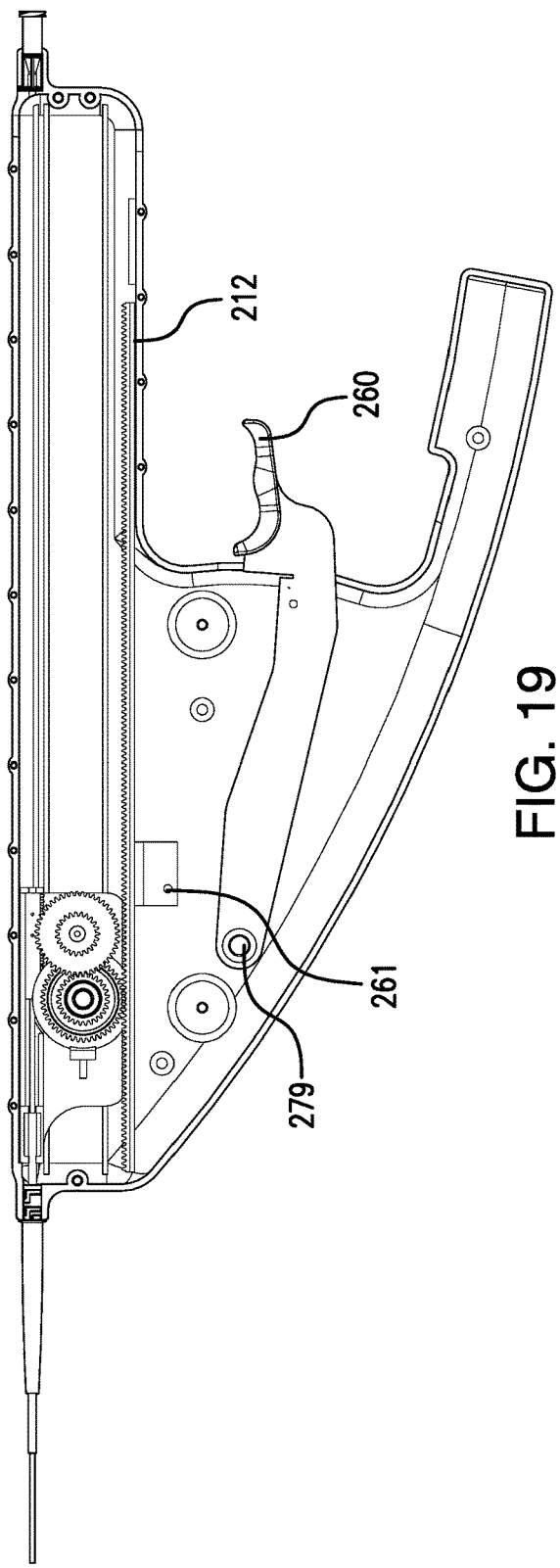
FIG. 19 is a right side view, with a portion of the handle housing removed, of the delivery system of FIG. 18.
Figure 20:
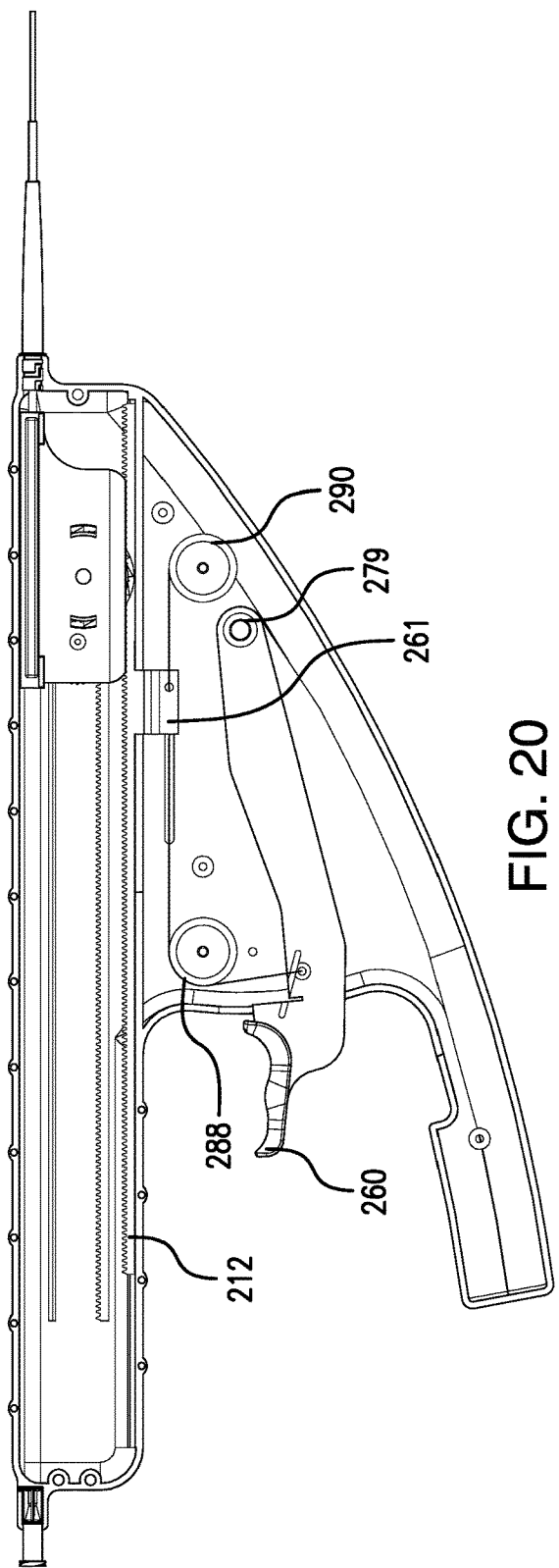
FIG. 20 is a left side view, with a portion of the handle housing removed, of the delivery system of FIG. 18.

In accordance with an alternative embodiment of the disclosed subject matter, a delivery system is provided wherein the trigger is coupled to the driving rack by a trigger pulley system. Referring now to FIG. 18 for the purpose of illustration and not limitation, an exemplary embodiment of a system for delivering an implant is provided and designated generally by reference character 1002. Portions of this exemplary embodiment are depicted in FIGS. 19 and 20. Elements that are similar to the previously described embodiment have been given like numbers. The delivery system 1002 can be configured to deliver an implant in a similar manner as described herein above.

The delivery system 1002 can include a handle 201, an outer tubular member 222, an inner shaft member 221, and an implant 223, for example, a braided implant. The handle 201 can include a trigger 260 and an actuation assembly 202, which can be configured to move the inner shaft member 221 and the outer tubular member 222 relative to the handle 201 as described above upon deployment of the trigger 260 from the first position to the second position and return from the second position to the first position. The trigger 260 can include a lock as described herein above.

The trigger 260 can be coupled to the driving rack 212 by a trigger pulley system. For example, the trigger 260 can be coupled to the handle at joint 279, which can be a pivot joint. The trigger 260 can be coupled to the slide 261 by a tether 288. The slide 261 can be coupled to the driving rack 212. The driving rack 212 can be fixedly coupled or releasably coupled to the slide 261. As an example and not by way of limitation, the driving rack 212 can have a bayonet-type engagement with the slide 261 (sometimes referred to herein as an intermediate element). Additionally, the slide can be coupled to a spring 290, for example, a constant force spring. The spring 290 can bias the slide toward a distal position and the trigger 260 in the first position. The spring can be supported in base 281. Additionally, the handle 201 can include a window 289 (FIG. 18), which can be used to manually move the slide.

In operation, the user can deploy the trigger 260 from the first position to the second position (referred to herein as the "first action"). The trigger 260 can pivot at the joint 279 (clockwise in FIG. 19). The tether 288 coupled to the trigger 260 and the slide 261 can pull the slide 261, and therefore the driving rack 212, proximally. The driving rack 212 can be functionally coupled to the actuation assembly, and can cause the inner shaft member 221 to move distally relative to the handle, and the outer tubular member 222 to move proximally relative to the handle. Thus, during the first action, the inner shaft member 221 can move distally relative to the handle 201 and the outer tubular member 222 can move proximally relative to the handle 201.

Upon return of the trigger 260 from the second position to the first position (herein referred to as the "second action"), which can be caused, for example, by the energy stored in the spring 290 pulling the slide 261 distally, the driving rack 212 can be moved distally. The driving rack 212 can be functionally coupled to the actuation assembly, and can cause the inner shaft member 221 to move proximally relative to the handle, and the outer tubular member 222 remain stationary relative to the handle. Thus, during the second action, the inner shaft member 221 moves proximally relative to the handle 201 and the outer tubular member 222 is stationary relative to the handle.

Figure 21:
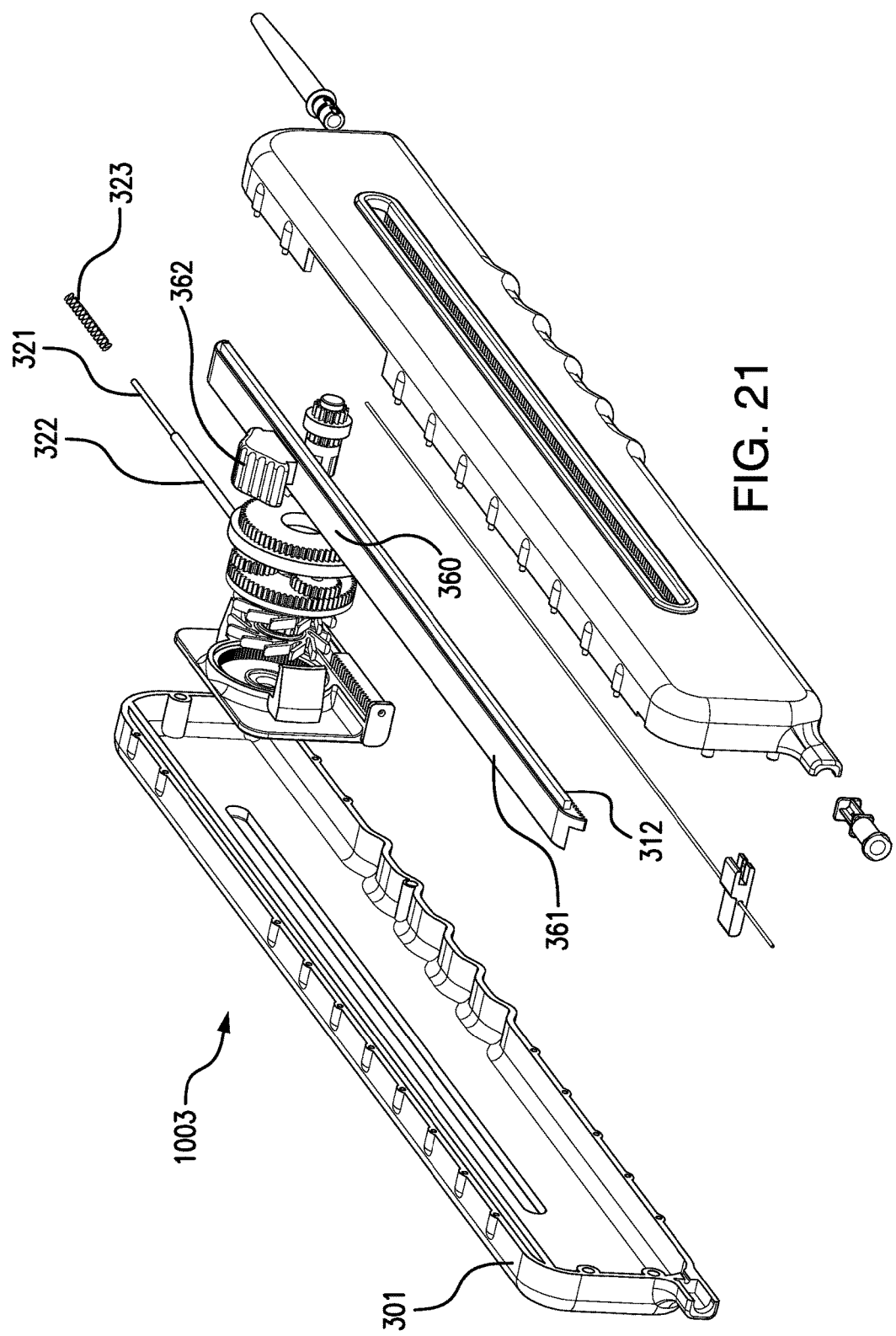
FIG. 21 is an exploded view of another exemplary embodiment of a delivery system in accordance with the disclosed subject matter.

Referring now to FIG. 21 for the purpose of illustration and not limitation, an exemplary embodiment of a system for delivering an implant is provided and designated generally by reference character 1003. Elements that are similar to the previously described embodiment have been given like numbers. The delivery system 1003 can be configured to deliver an implant in a similar manner as described herein above.

The delivery system 1003 can include a handle 301, an outer tubular member 322, an inner shaft member 321, and an implant 323, for example, a braided implant. The handle 301 can include a trigger 360 and an actuation assembly 302, which can be configured to move the inner shaft member 321 and the outer tubular member 322 relative to the handle 301 as described above upon deployment of the trigger 360 from the first position to the second position and return from the second position to the first position. The trigger 360 can include a lock as described herein above.

The trigger 360 can include a slide 361 that can include an engagement surface 362 to be engaged by the user. The driving rack 312 can be fixedly coupled or releasably coupled to the slide 361. As an example and not by way of limitation, the driving rack 312 and the slide 361 can be a unitary member. The trigger 360 can be coupled to a spring, which can bias the trigger 360 toward the first position.

During operation, the user can deploy the trigger 360 from the first position to the second position (referred to herein as the "first action"). The trigger, and therefore the slide 361 and the driving rack 312, can move in a proximal direction. The driving rack 312 can be functionally coupled to the actuation assembly, and can cause the inner shaft member 321 to move distally relative to the handle, and the outer tubular member 322 to move proximally relative to the handle. Thus, during the first action, the inner shaft member 321 can move distally relative to the handle 301 and the outer tubular member 322 can move proximally relative to the handle 301.

Upon return of the trigger 360 from the second position to the first position (hereinafter referred to as the "second action"), the trigger 360, and therefore the slide 361 and the driving rack 312 can move in a distally relative to the handle 301. The driving rack 312 can be functionally coupled to the actuation assembly, and can cause the inner shaft member 321 to move proximally relative to the handle, and the outer tubular member 322 remain stationary relative to the handle. Thus, during the second action, the inner shaft member 321 moves proximally relative to the handle 301 and the outer tubular member 322 is stationary relative to the handle.

Figure 22:
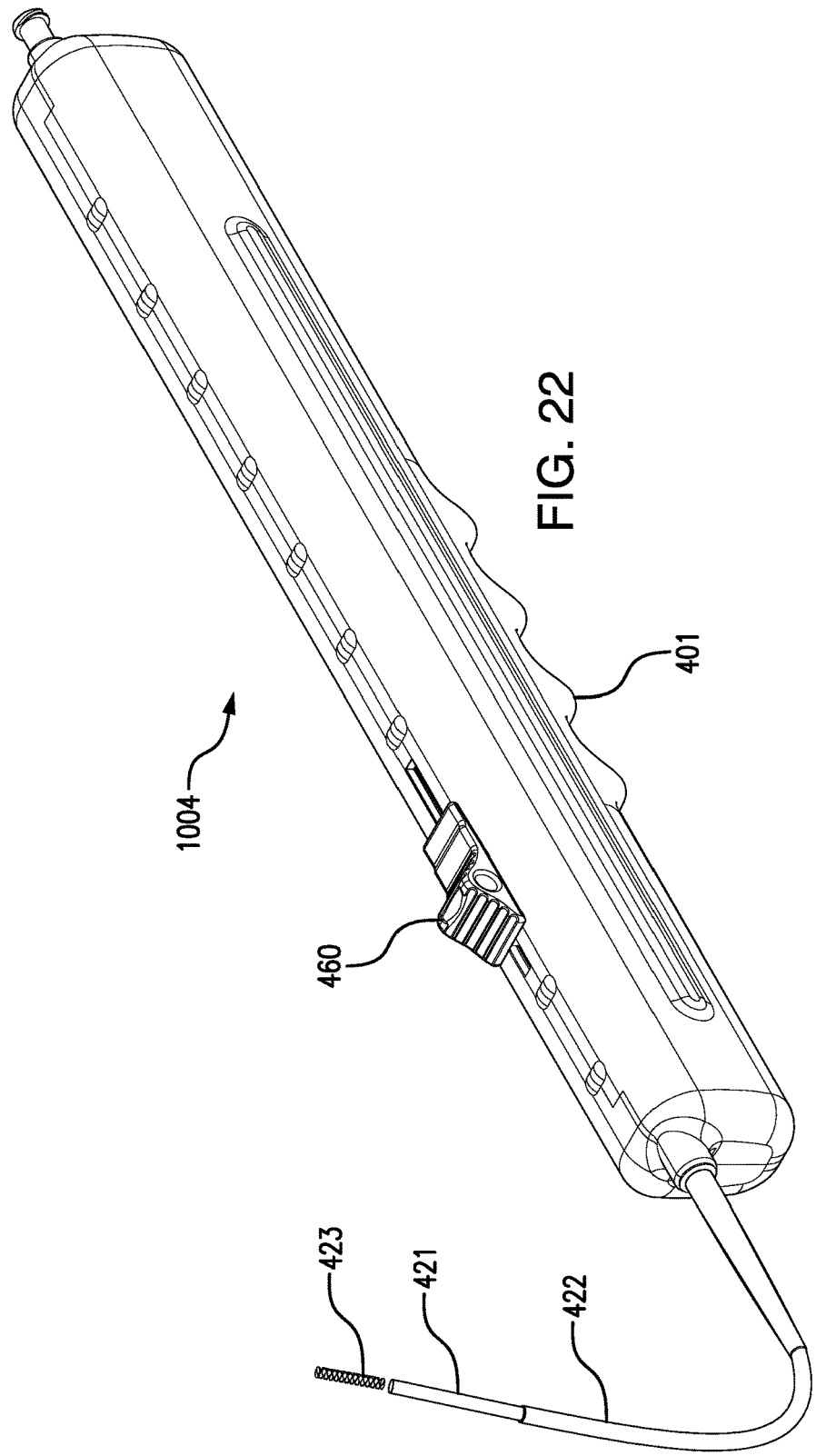
FIG. 22 is a perspective view of a yet another exemplary embodiment of a delivery system in accordance with the disclosed subject matter.
Figure 23:
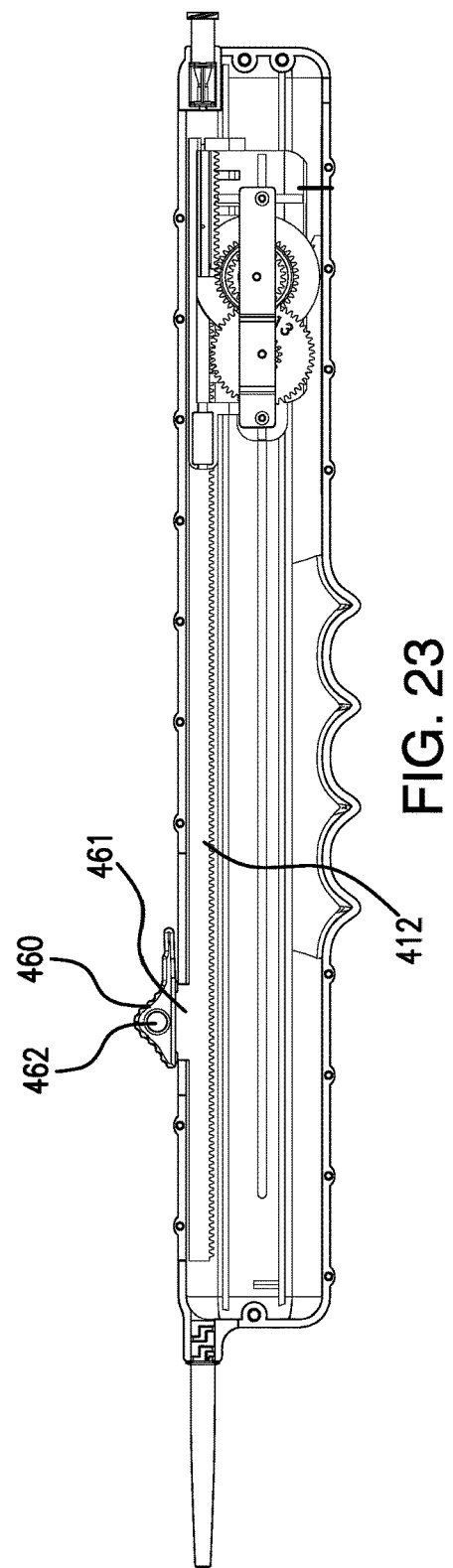
FIG. 23 is a right side view, with a portion of the handle housing removed, of the delivery system of FIG. 22.
Figure 24:
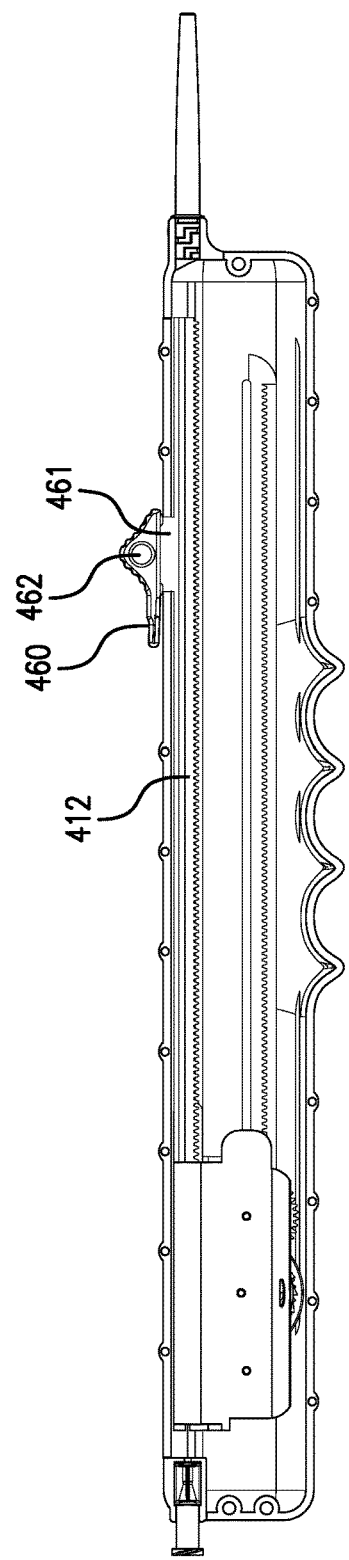
FIG. 24 is a left side view, with a portion of the handle housing removed, of the delivery system of FIG. 22.

Referring now to FIG. 22 for the purpose of illustration and not limitation, an exemplary embodiment of a system for delivering an implant is provided and designated generally by reference character 1004. Portions of this exemplary embodiment are depicted in FIGS. 23 and 24. Elements that are similar to the previously described embodiment have been given like numbers. The delivery system 1004 can be configured to deliver an implant in a similar manner as described herein above.

The delivery system 1004 can include a handle 401, an outer tubular member 422, an inner shaft member 421, and an implant 423, for example, a braided implant. The handle 401 can include a trigger 460 and an actuation assembly 402, which can be configured to move the inner shaft member 421 and the outer tubular member 422 relative to the handle 401 as described above upon deployment of the trigger 460 from the first position to the second position and return from the second position to the first position. The trigger 460 can include a lock as described herein above.

The trigger 460 can include a slide 461 that can include an engagement surface 462 to be engaged by the user. The driving rack 412 can be fixedly coupled or releasably coupled to the slide 461. As an example and not by way of limitation, the driving rack 412 and the slide 461 can be a unitary member. The trigger 460 can be coupled to a spring, which can bias the trigger 460 toward the first position.

During operation, the user can deploy the trigger 460 from the first position to the second position (referred to herein as the "first action"). The trigger, and therefore the slide 461 and the driving rack 412, can move in a distal direction. The driving rack 412 can be functionally coupled to the actuation assembly, and can cause the inner shaft member 421 to move distally relative to the handle, and the outer tubular member 422 to move proximally relative to the handle. Thus, during the first action, the inner shaft member 421 can move distally relative to the handle 301 and the outer tubular member 422 can move proximally relative to the handle 401.

Upon return of the trigger 460 from the second position to the first position (herein referred to as the "second action"), the trigger 460, and therefore the slide 461 and the driving rack 412 can move in a proximal relative to the handle 401. The driving rack 412 can be functionally coupled to the actuation assembly, and can cause the inner shaft member 421 to move proximally relative to the handle, and the outer tubular member 422 remain stationary relative to the handle. Thus, during the second action, the inner shaft member 421 moves proximally relative to the handle 401 and the outer tubular member 422 is stationary relative to the handle.

Figure 25:
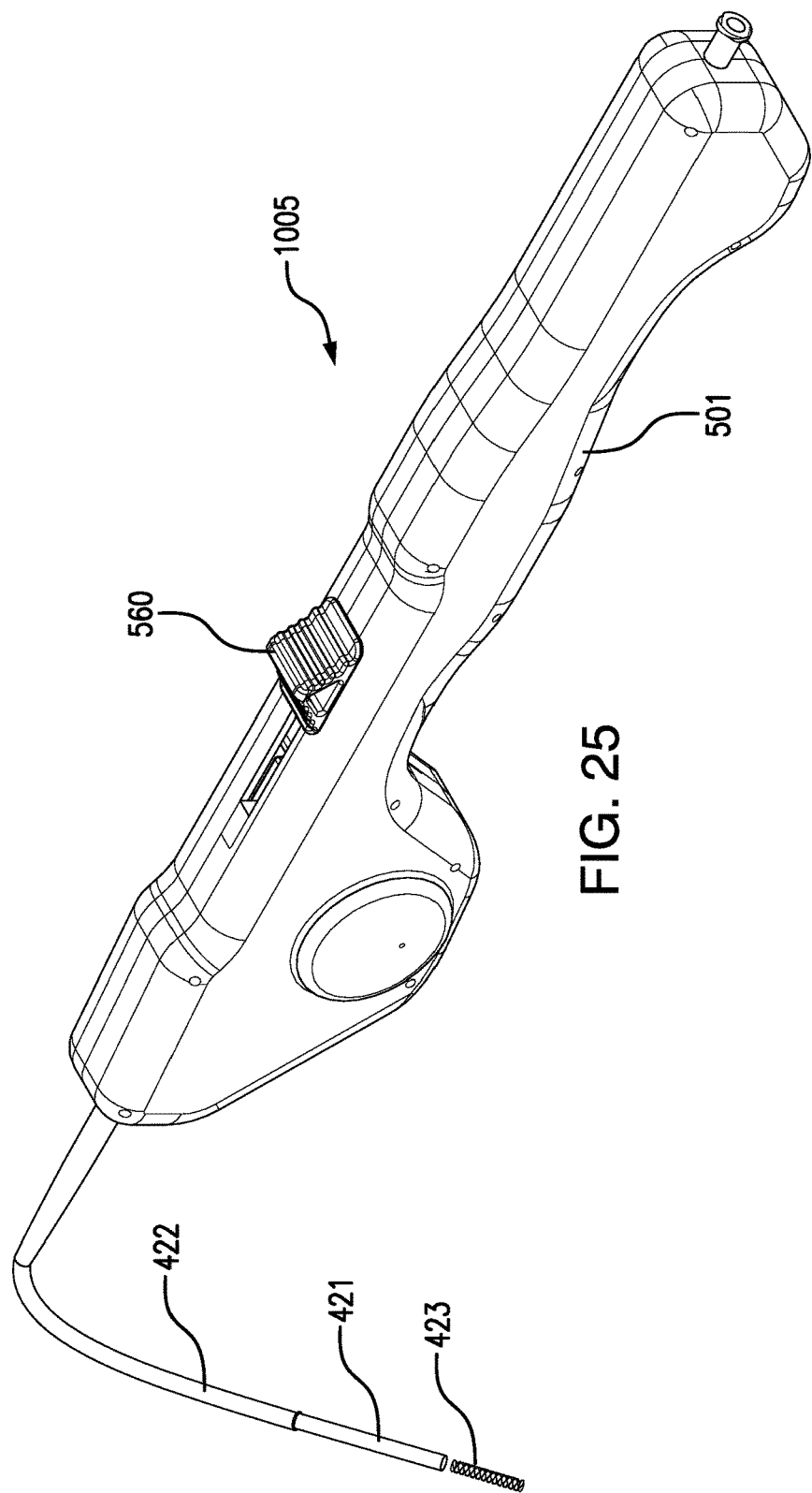
FIG. 25 is a perspective view of another exemplary embodiment of a delivery system in accordance with the disclosed subject matter.
Figure 26:
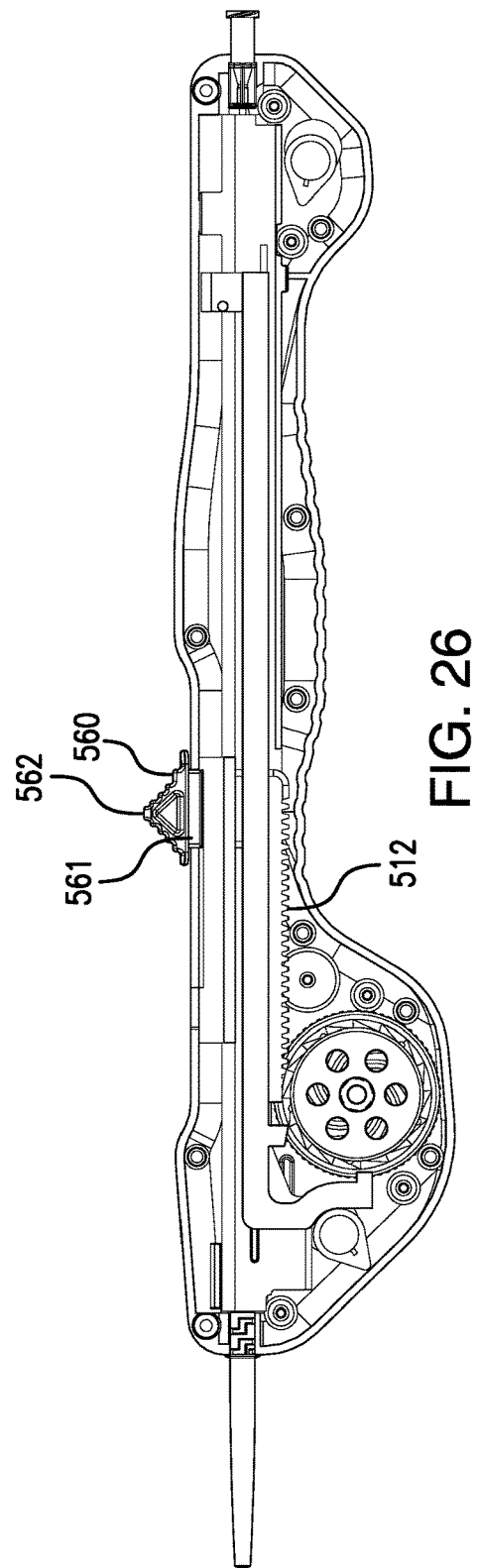
FIG. 26 is a right side view, with a portion of the handle housing removed, of the delivery system of FIG. 25.
Figure 27:
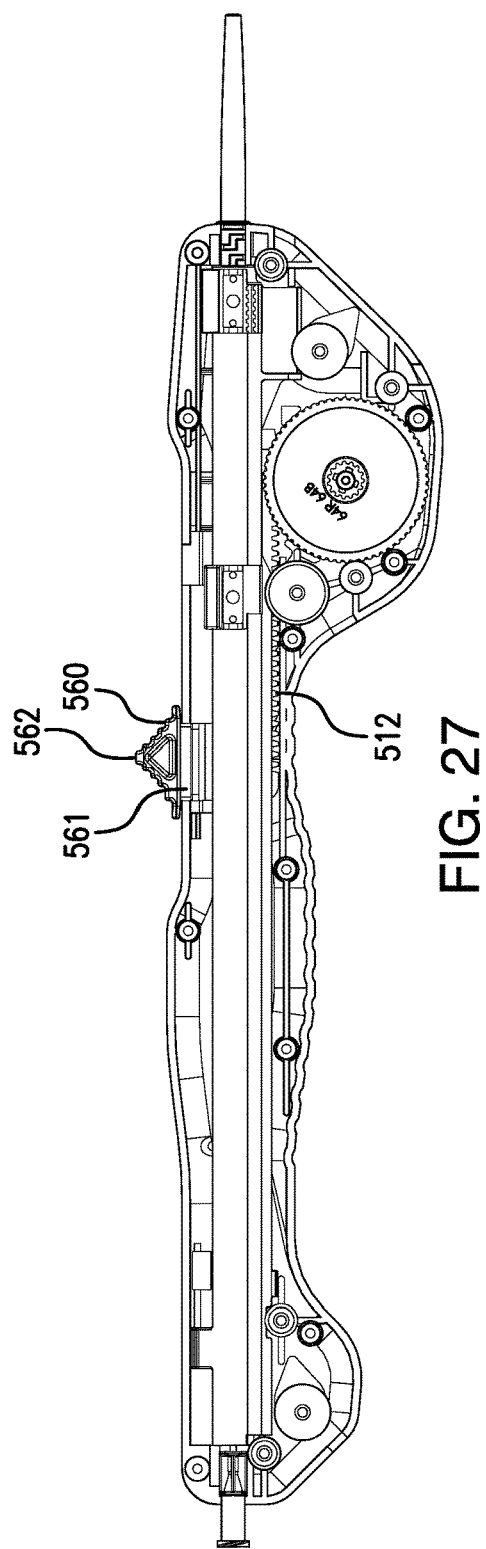
FIG. 27 is a left side view, with a portion of the handle housing removed, of the delivery system of FIG. 25.

Referring now to FIG. 25 for the purpose of illustration and not limitation, an exemplary embodiment of a system for delivering an implant is provided and designated generally by reference character 1005. Portions of this exemplary embodiment are depicted in FIGS. 26 and 27. Elements that are similar to the previously described embodiment have been given like numbers. The delivery system 1005 can be configured to deliver an implant in a similar manner as described herein above.

The delivery system 1005 can include a handle 501, an outer tubular member 522, an inner shaft member 521, and an implant 523, for example, a braided implant. The handle 501 can include a trigger 560 and an actuation assembly 502, which can be configured to move the inner shaft member 521 and the outer tubular member 522 relative to the handle 501 as described above upon deployment of the trigger 560 from the first position to the second position and return from the second position to the first position. The trigger 560 can include a lock as described herein above.

The trigger 560 can include a slide 561 that can include an engagement surface 562 to be engaged by the user. The driving rack 512 can be fixedly coupled or releasably coupled to the slide 561. As an example and not by way of limitation, the driving rack 512 and the slide 561 can be a unitary member. The trigger 560 can be coupled to a spring, which can bias the trigger 560 toward the first position.

During operation, the user can deploy the trigger 560 from the first position to the second position (referred to herein as the "first action"). The trigger, and therefore the slide 561 and the driving rack 512, can move in a distal direction. The driving rack 512 can be functionally coupled to the actuation assembly, and can cause the inner shaft member 521 to move distally relative to the handle, and the outer tubular member 522 to move proximally relative to the handle. Thus, during the first action, the inner shaft member 521 can move distally relative to the handle 501 and the outer tubular member 522 can move proximally relative to the handle 501.

Upon return of the trigger 560 from the second position to the first position (herein referred to as the "second action"), the trigger 560, and therefore the slide 561 and the driving rack 512 can move in a proximal relative to the handle 501. The driving rack 512 can be functionally coupled to the actuation assembly, and can cause the inner shaft member 521 to move proximally relative to the handle, and the outer tubular member 522 remain stationary relative to the handle. Thus, during the second action, the inner shaft member 521 moves proximally relative to the handle 501 and the outer tubular member 522 is stationary relative to the handle.

The embodiments described above can be formed of any suitable materials, for example, the handle and actuation assembly elements can be made from plastic, composites, or metal. The handle housing portion can be made from glass filled plastics or other plastic resins, for example ADS, polycarbonate, or an ADS polycarbonate blend. A rubber overmold can be used for grip and aesthetics, for example, on the trigger and the handle body. The strain relief can be a soft plastic, for example, polyethylene. The trigger and related elements can be formed by silicon impregnated poly oxymethylene or acetal (e.g., DelRin® sold by DuPont). The various pins and springs can be formed from plastic, metal (e.g., stainless steel or aluminum), or music wire. Spring dampers can be made of UNA, EPVM, Silicon, Eurothane, or Santoprene.

While the disclosed subject matter is described herein in terms of certain preferred embodiments for purpose of illustration and not limitation, those skilled in the art will recognize that various modifications and improvements can be made to the disclosed subject matter without departing from the scope thereof. Moreover, although individual features of one embodiment of the disclosed subject matter can be discussed herein or shown in the drawings of one embodiment and not in other embodiments, it should be readily apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other possible combinations. Thus, the foregoing description of specific embodiments of the disclosed subject matter has been presented for purposes of illustration and description. It is not intended to be exhaustive or to limit the disclosed subject matter to those embodiments disclosed.

The following Applications, which are filed on the same day as this application, are incorporated by reference in their entirety: U.S. patent application Ser. No. 14/932,848; U.S. patent application Ser. No. 14/932,875; U.S. patent application Ser. No. 14/932,862; U.S. patent application Ser. No. 14/932,884; U.S. patent application Ser. No. 14/932,795; U.S. patent application Ser. No. 14/932,805; U.S. patent application Ser. No. 14/932,900; PCT Patent Application No. PCT/US2015/059070; PCT Patent Application No. PCT/US2015/059074; and PCT Patent Application No. PCT/US2015/059084.

Furthermore, it is recognized that the actuation assembly and delivery system as disclosed herein can be used in a method of delivering an implant. That is, for purpose of illustration, such method would include providing a delivery system as disclosed herein, positioning the distal end portion of the outer tubular member proximate a desired site, and deploying the delivery system to push the implant from the outer tubular member to the desired site.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The invention claimed is:

1. A trigger assembly for an implant delivery system having an outer tubular member and an inner shaft member, the inner shaft member being disposed within the outer tubular member and movable distally and proximally relative to the outer tubular member and an actuation assembly configured to displace the inner shaft member distally and proximally relative to the outer tubular member:
   a trigger functionally connected to the actuation assembly by a driving rack; and
   a gear train functionally disposed between the trigger and the driving rack;
   wherein the gear train comprises
      a trigger gear sector,
      a trigger pinion operatively meshed with the trigger gear sector,
      a slide pinion operatively coupled to the trigger pinion, and
      a slide rack disposed on a slide coupled to the driving rack and operatively meshed with the slide pinion,
   wherein the driving rack is configured to move the inner shaft member distally relative the handle and the outer tubular member proximally relative the handle.

2. The trigger assembly of claim 1, wherein the driving rack is fixedly coupled to the slide.

3. The trigger assembly of claim 1, wherein the driving rack is detachably coupled to the slide.

4. The trigger assembly of claim 1, further comprising a ratchet mechanism functionally coupled to the trigger.

5. The trigger assembly of claim 4, wherein the ratchet mechanism comprises a first state configured to allow the trigger to move toward a second position and prohibit motion toward a first position.

6. The trigger assembly of claim 4, wherein the ratchet mechanism comprises a second state configured to allow the trigger to move toward a first position and prohibit motion toward a second position.

7. The trigger assembly of claim 4, where in the ratchet mechanism comprises a first pawl and a trigger ratchet rack configured to engage the pawl to permit unidirectional motion of the slide.

8. The trigger assembly of claim 7, wherein the pawl comprises a first state wherein the pawl engages the trigger ratchet rack to permit unidirectional motion of the slide in a first direction.

9. The trigger assembly of claim 8, wherein the ratchet mechanism further comprises a second pawl having a first state wherein the second pawl engages the ratchet rack to permit unit-direction motion of the slide in a second direction.

10. The trigger assembly of claim 9, wherein the first and second pawl each have a second state wherein the first and second pawl do not engage the trigger ratchet rack, and
   wherein when the first pawl is in the first state the second pawl is in the second state and when the second pawl is in the first state the first pawl is in the second state.

11. The trigger assembly of claim 10, wherein the ratchet mechanism further comprises a ratchet trip coupled to the first and second pawls.

12. The trigger assembly of claim 11, wherein as the trigger approaches the second position from the first position the ratchet trip causes the first pawl to switch from the first state to the second state and the ratchet trip causes the second pawl to switch from the second state to the first state.

13. The trigger assembly of claim 11, wherein as the trigger approaches the first position from the second position the ratchet trip causes the first pawl to switch from the second state to the first state and the ratchet trip causes the second pawl to switch from the first state to the second state.

14. The trigger assembly of claim 7, wherein the pawl comprises a second state wherein the pawl engages the trigger ratchet rack to permit unidirectional motion of the slide in a second direction.

15. The trigger assembly of claim 14, wherein the pawl is configured to switch from the first state to the second state as the trigger approaches the second position from the first position.

16. The trigger assembly of claim 15, wherein the pawl is configured to switch from the second state to the first state as the trigger approaches the first position from the second position.

17. The trigger assembly of claim 14, wherein the pawl is configured to be disengaged with the trigger ratchet rack by urging the pawl away from the trigger ratchet rack.

18. The trigger assembly of claim 17, wherein the pawl is biased toward engagement with the trigger ratchet rack.

* * * * *